(12) United States Patent
Benson et al.

(10) Patent No.: US 11,384,093 B2
(45) Date of Patent: Jul. 12, 2022

(54) PROCESS FOR PREPARING 2-EXO-(2-METHYLBENZYLOXY)-1-METHYL-4-ISOPROPYL-7-OXABICYCLO[2.2.1]HEPTANE

(71) Applicant: BASF Agro B.V., Arnhem (NL)

(72) Inventors: Stefan Benson, Ludwigshafen (DE);
Michael Rack, Ludwigshafen (DE);
Christiane Alznauer, Ludwigshafen (DE); Roland Goetz, Ludwigshafen (DE); Bernd Wolf, Ludwigshafen (DE)

(73) Assignee: BASF AGRO B.V., Arnhem (NL)

( * ) Notice: Subject to any disclaimer, the term of this patent is extended or adjusted under 35 U.S.C. 154(b) by 465 days.

(21) Appl. No.: 16/498,625

(22) PCT Filed: Mar. 23, 2018

(86) PCT No.: PCT/EP2018/057397
§ 371 (c)(1),
(2) Date: Sep. 27, 2019

(87) PCT Pub. No.: WO2018/177907
PCT Pub. Date: Oct. 4, 2018

(65) Prior Publication Data
US 2020/0031842 A1 Jan. 30, 2020

(30) Foreign Application Priority Data

Mar. 31, 2017 (EP) ..................... 17164278

(51) Int. Cl.
*C07D 493/08* (2006.01)
*A01N 25/02* (2006.01)
*A01N 43/90* (2006.01)
(52) U.S. Cl.
CPC .......... *C07D 493/08* (2013.01); *A01N 25/02* (2013.01); *A01N 43/90* (2013.01)
(58) Field of Classification Search
CPC .................................................. C07D 493/18
See application file for complete search history.

(56) References Cited

U.S. PATENT DOCUMENTS

| 4,487,945 A | 12/1984 | Payne |
| 4,542,244 A | 9/1985 | Payne et al. |
| 4,670,041 A | 6/1987 | Payne et al. |
| 2018/0134641 A1 | 5/2018 | Wolf et al. |
| 2018/0141924 A1 | 5/2018 | Wolf et al. |
| 2019/0071377 A1 | 3/2019 | Wolf et al. |

FOREIGN PATENT DOCUMENTS

| CN | 101602770 B | 5/2011 |
| EP | 0081893 A2 | 6/1983 |
| WO | WO-2016/180614 A1 | 11/2016 |
| WO | WO-2016/180642 A1 | 11/2016 |
| WO | WO-2017/144336 A1 | 8/2017 |
| WO | WO-2017/144337 A1 | 8/2017 |

(Continued)

OTHER PUBLICATIONS

Shah et al. Tetrahedron Lett. 2002, 43, 8603-8606 (Year: 2002).*

(Continued)

*Primary Examiner* — Amanda L. Aguirre
(74) *Attorney, Agent, or Firm* — Marshall, Gerstein & Borun LLP

(57) ABSTRACT

This invention relates to a process for preparing (±)-2-exo-(2-Methylbenzyloxy)-1-methyl-4-iso-propyl-7-oxabicyclo[2.2.1]heptane of the formula (I)

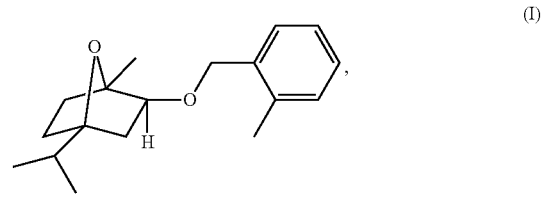

any of its individual enantiomers or any non-racemic mixture thereof, comprising the step of reacting (±)-2-exo-hydroxy-1-methyl-4-isopropyl-7-oxabicyclo[2.2.1]heptane of the formula (II)

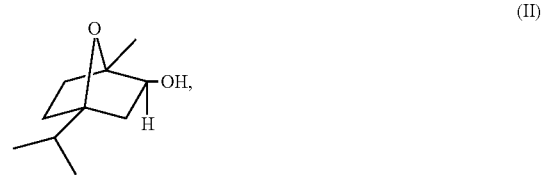

any of its individual enantiomers or any non-racemic mixture thereof with a 2-Methylbenzyl compound of the formula (III)

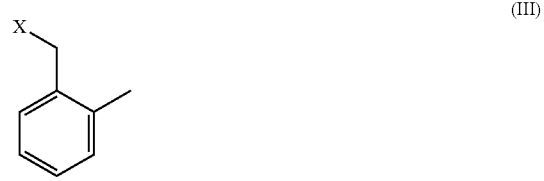

wherein X is a leaving group, in the presence of at least one base, at least one catalyst selected from rubidium salts, cesium salts and any combination thereof and at least one inert organic solvent S1.

14 Claims, No Drawings

(56) References Cited

FOREIGN PATENT DOCUMENTS

| WO | WO-2017/215928 A1 | 12/2017 |
|----|-------------------|---------|
| WO | WO-2017/215929 A1 | 12/2017 |
| WO | WO-2018/050518 A1 | 3/2018 |
| WO | WO-2018/149676 A1 | 8/2018 |

OTHER PUBLICATIONS

Shah et al. Tetrahedron 2005, 61,6652-6656 (Year: 2005).*
"The Pesticide Manual", ed. C.D.S. Tomlin, British Crop Production Council, Fourteenth Edition, 2006, pp. 195-196.
Barton, et al., "Herbicidal Activity of Cineole Derivatives", Journal of Agricultural and Food Chemistry, vol. 58, Issue 18, Sep. 22, 2010, pp. 10147-10155.
Galli, "Cesium ion effect and macrocyclization. A critical review", Organic Preparations and Procedures International, vol. 24, Issue 3, Feb. 11, 1992, pp. 285-307.
European Search Report for EP Application No. 17164278.8, dated May 22, 2017, 3 pages.
International Search Report and Written Opinion for PCT Patent Application No. PCT/EP2018/057397, dated May 4, 2018.
Lee, et al., "Metabolic fate of cinmethylin in rats", Journal of Agricultural and Food Chemistry, vol. 34, Issue 2, Mar. 1, 1986, pp. 162-170.
Silvestre, et al., "Synthesis of Some New Benzylic Ethers from 1,8-Cineole with Antimicrobial Activity", Chemical Monthly, vol. 130, Issue 4, 1999, pp. 589-595.
Zhou, et al., "Synthesise of Alkly Aryl Ethers Cesium Carbonate Catalyzed O-Alkylation of Phenol to", Journal of Hunan University (Natural Sciences), vol. 34, Issue 3, Mar. 2007, pp. 64-66.

* cited by examiner

PROCESS FOR PREPARING 2-EXO-(2-METHYLBENZYLOXY)-1-METHYL-4-ISOPROPYL-7-OXABICYCLO[2.2.1]HEPTANE

This application is a National Stage application of International Application No. PCT/EP2018/057397 filed Mar. 23, 2018. This application also claims priority under 35 U.S.C. § 119 to European Patent Application No. 17164278.8, filed Mar. 31, 2017.

This invention relates to a process for preparing (±)-2-exo-(2-Methylbenzyloxy)-1-methyl-4-iso-propyl-7-oxabicyclo[2.2.1]heptane of the formula (I), any one of its individual enantiomers or any non-racemic mixture thereof by reacting (±)-2-exo-hydroxy-1-methyl-4-isopropyl-7-oxabicyclo[2.2.1]heptane of the formula (II), any one of its individual enantiomers or any non-racemic mixture thereof with a 2-Methylbenzyl compound of the formula (III) in the presence of a base and an organic solvent.

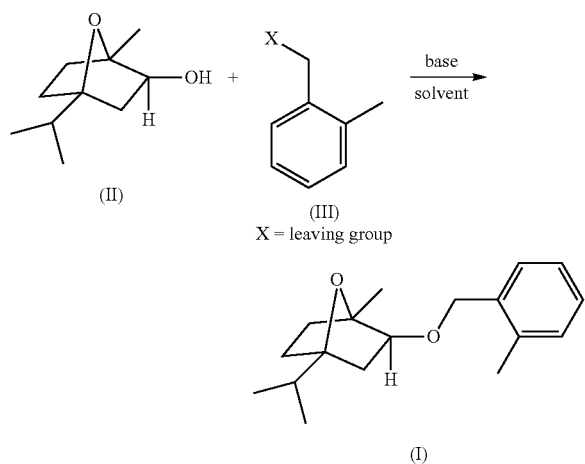

The racemic mixture (±)-2-exo-(2-Methylbenzyloxy)-1-methyl-4-isopropyl-7-oxabicyclo[2.2.1]heptane is a known herbicidal compound which has been developed for use in rice. It is described in the The Pesticide Manual, Fourteenth Edition, Editor: C. D. S. Tomlin, British Crop Production Council, 2006, entry 157, pages 195-196 with its common name Cinmethylin, its IU-PAC name (1RS,2SR,4SR)-1,4-epoxy-p-menth-2-yl 2-methylbenzyl ether and its Chemical Abstracts name exo-(±)-1-methyl-4-(1-methylethyl)-2-[(2-methylphenyl)methoxy]-7-oxabicyclo[2.2.1]heptane.

The racemic mixture (±)-2-exo-(2-M ethylbenzyloxy)-1-methyl-4-isopropyl-7-oxabicyclo[2.2.1]heptane (herein also referred to as the "exo-(±)-isomers", CAS RN 87818-31-3)

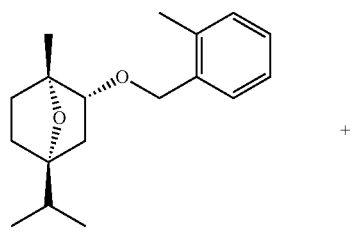

+

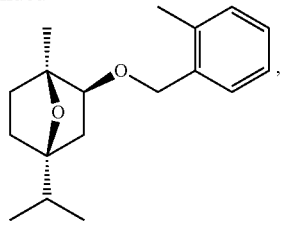

contains equal parts of the two enantiomers (+)-2-exo-(2-Methylbenzyloxy)-1-methyl-4-isopropyl-7-oxabicyclo[2.2.1]heptane (herein also referred to as the "exo-(+)-isomer", CAS RN 87818-61-9) and (−)-2-exo-(2-M ethylbenzyloxy)-1-methyl-4-isopropyl-7-oxabicyclo[2.2.1]heptane (herein also referred to as the "exo-(−)-isomer", CAS RN 87819-60-1).

The preparation of (±)-2-exo-(2-Methylbenzyloxy)-1-methyl-4-isopropyl-7-oxabicyclo[2.2.1]heptane and its exo-(+)-isomer and exo-(−)-isomer by reacting (±)-2-exo-hydroxy-1-methyl-4-isopropyl-7-oxabicyclo[2.2.1]heptane with 2-methylbenzyl chloride in the presence of sodium hydride as a base and dimethylformamide as organic solvent has been described in EP 0 081 893 A2 (see Examples 29, 34, 35 and 62), U.S. Pat. No. 4,487,945 (see Embodiment 48), U.S. Pat. No. 4,542,244 (see Embodiment 219) and U.S. Pat. No. 4,670,041 (see Embodiment 219).

The preparation of the exo-(−)-isomer by reacting (−)-2-exo-hydroxy-1-methyl-4-isopropyl-7-oxa-bicyclo[2.2.1]heptane with 2-methylbenzyl chloride in the presence of sodium hydride as a base and N,N-dimethylacetamide as organic solvent has been described in U.S. Pat. No. 4,487,945 (see Embodiment 46), U.S. Pat. No. 4,542,244 (see Embodiment 218) and U.S. Pat. No. 4,670,041 (see Embodiment 218).

CN 101602770 A describes a three-step synthesis for the preparation of Cinmethylin. In steps 1 and 2, terpinen-4-ol is converted to the corresponding 1,2-epoxide which is then subjected to isomerization to give the 1,2-epoxide isomerization product. In final step 3, Cinmethylin is obtained by condensation of the 1,2-epoxide isomerization product in the presence of various combinations of bases and organic solvents (see Examples 1, 2, 3, 8 and 9: sodium hydroxide/ethyl acetate; Examples 4 and 5: sodium amide/dichloromethane; Example 6: sodium hydride/benzene and Example 7: sodium tert-butoxide/toluene).

Silvestre et al., Monatshefte für Chemie 130, pages 589-595 (1999) describes the synthesis of benzylic ether derivatives of 1,8-cineole by refluxing 3-exo-hydroxy-1,8-cineole with benzyl chloride or derivatives thereof in the presence of sodium hydride in dry tetrahydrofuran.

Barton et al., J. Agric. Food Chem. 2010, 58, pages 10147-10155 describes the preparation of cinmethylin by a method analogous to that reported in Silvestre at al. (see above), i.e. by reacting (±)-2-exo-hydroxy-1-methyl-4-isopropyl-7-oxabicyclo[2.2.1]heptane (which is referred to as "alcohol 10") with 2-methylbenzyl chloride in the presence of sodium hydride in dry tetrahydrofuran.

The aforementioned processes for preparing (±)-2-exo-(2-Methylbenzyloxy)-1-methyl-4-isopropyl-7-oxabicyclo[2.2.1]heptane that utilize sodium hydride and sodium amide as bases suffer from the drawback that these substances are dangerously reactive in the presence of small quantities of oxygen or moisture. Such reactions may lead to the formation of hazardous gases such as hydrogen ($H_2$) or ammonia ($NH_3$). Thus, not only appropriate care and precautions should be exercised during handling and storage of these substances but also specific safety measures such as, for example, an inert gas atmosphere (e.g. nitrogen), proper cooling, removal of the hazardous gases ($H_2$, $NH_3$) and dilution are required during the course of the reaction.

Further, the combined use of sodium hydroxide and ethyl acetate as described in CN 101602770 A (see Examples 1, 2, 3, 8 and 9) may lead to the hydrolysis of the solvent ethyl acetate in view of the fact that sodium hydroxide is commonly used as base in the saponification of esters. This implies the formation of relatively high amounts of undesired by-products, low yields and loss of valuable solvent which is not available for recycling.

Philip W. Lee et al., Journal of Agricultural and Food Chemistry, Vol. 34, No. 2, 1986, pages 162-170 discloses the preparation of a proposed cinmethylin metabolite, i.e. exo-2-[[2-(Chloromethyl)phenyl]methoxy]-1-methyl-4-(1-methylethyl)-7-oxabicyclo [2.2.1]heptane, by refluxing a solution of exo-1-methyl-4-(1-methylethyl)-7-oxabicyclo-[2.2.1]heptan-2-ol] in toluene and powdered sodium hydroxide under a Stark-Dean trap until no more water was removed. The resulting solution was subsequently reacted with α,α-dichloro-o-xylene to give a ca. 50:50 mixture of the mono- and disubstitution products along with the unreacted dichloroxylene. Purification of the reaction mixture gave exo-2-[[2-(Chloromethyl)phenyl]methoxy]-1-methyl-4-(1-methylethyl)-7-oxabicyclo[2.2.1] heptane in a low yield of 30%.

Carlo Galli, Organic Preparations and Procedures International, 24(3), 1992, pages 285-307 discusses the use of cesium salts in organic synthesis, inter alia the use of cesium carbonate as heterogenous base in nucleophilic displacement reactions run in dipolar aprotic solvents such as dimethylformamide (DMF) with anionic nucleophiles.

Zhou Bing et al., Journal of Hunan University (Natural Sciences), Vol. 34, No. 3, March 2007, pages 64 to 66, discloses reactions of a phenolic compound, such as phenol, naphthol, 3,5-di(tert-butyl)phenol and 4-[di(4-tert-butylphenyl)phenylmethyl]phenol), with a halogenated hydrocarbon, such as bromoethane, bromobutane and benzyl bromide, for the preparation of the corresponding alkyl aryl ether under the conditions of using cesium carbonate as the catalyst, potassium hydroxide as the base, dimethylformamide (DMF) as the solvent, at room temperature and in the presence of a molecular sieve.

One of the disadvantages of the aforementioned methods that utilize cesium carbonate lies in the combined use with dimethylformamide as solvent. Due to its reprotoxic properties dimethyl-formamide has been included in the Candidate List of Substances of Very High Concern by the European Chemicals Agency (ECHA). Thus, specific safety measures such as personal protective equipment and closed processes with proper exposure controls must be followed during handling and use of this substance. Further, dimethylformamide is hydrolyzed by strong bases such as sodium or potassium hydroxide, especially at elevated temperatures, which leads to relatively high amounts of undesired by-products, low yields and loss of valuable solvent. Another drawback of the reaction disclosed in Zhou Bing et al. is that the reaction is conducted in the presence of a molecular sieve which involves additional measures on a large scale such as passing the reactants over a molecular sieve bed which must be periodically regenerated.

Moreover, both the relatively high access amounts of the halogenated hydrocarbon and the relatively high amounts of the catalyst cesium carbonate in relation to the phenolic compound cause the formation of undesirable side components.

The aforementioned disadvantages make the prior art processes not very suitable for an industrial scale production and unattractive for economic, environmental and working-health reasons.

In view of the above drawbacks, there is still need for an improved process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which would not only make the synthesis safe and environmentally friendly, but also would be simple and cost-effective for commercial utilization.

It is therefore an object of the present invention to overcome or ameliorate at least one of the above disadvantages and thus to provide an improved and more economically and commercially feasible process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof.

Another object is to provide an industrially simple process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which gives the desired final product in good yields.

A further object is to provide a more environmentally friendly process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, by reducing unfavorable environmental effects.

Still another object is to provide an industrially feasible process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which reduces safety concerns and the existence of hazardous conditions.

Yet another object is to provide a process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which reduces the formation of undesirable by-products.

It has now surprisingly been found that these and further objects are, in part or in whole, achieved by a process for preparing (±)-2-exo-(2-Methylbenzyloxy)-1-methyl-4-isopropyl-7-oxa-bicyclo[2.2.1]heptane of the formula (I)

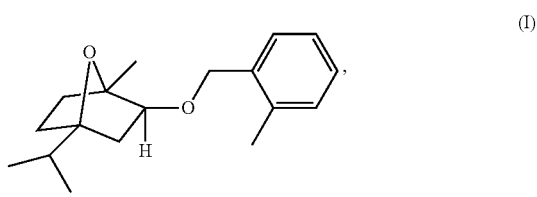 [SMILES: Cc1ccccc1COC1CC2(C(C)C)CCC1(C)O2]

(I)

any of its individual enantiomers or any non-racemic mixture thereof comprising the step of reacting (±)-2-exo-hydroxy-1-methyl-4-isopropyl-7-oxabicyclo[2.2.1]heptane of the formula (II)

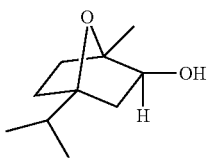
(II)

with a 2-Methylbenzyl compound of the formula (III)

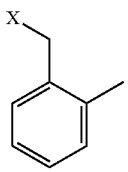
(III)

wherein X is a leaving group, in the presence of at least one base, at least one catalyst selected from rubidium salts, cesium salts and any combination thereof and at least one inert organic solvent S1.

Accordingly, the aforementioned process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof is a subject matter of the present invention.

The process according to the present invention entails a series of advantages and overcomes drawbacks of the prior art processes.

The process of this invention does not utilize dangerous substances such as alkali metal hydrides (e.g. sodium hydride) or amides (e.g. sodium amide) thus minimizing the existence of hazardous reaction conditions and the need for safety measures and equipment while maintaining efficiency and ease of operations.

In particular, it has surprisingly been found that the use of only catalytic amounts of a rubidium and/or cesium salt can effectively catalyze the reaction of (±)-2-exo-hydroxy-1-methyl-4-isopropyl-7-oxabicyclo[2.2.1]heptane (II) with the 2-Methylbenzyl compound (III) for the preparation of (±)-2-exo-(2-Methylbenzyloxy)-1-methyl-4-isopropyl-7-oxabicyclo[2.2.1]heptane (I) in the presence of a base and an organic solvent. This is a quite astonishing result in view of the fact that the acidity of alcohols such as (±)-2-exo-hydroxy-1-methyl-4-isopropyl-7-oxabicyclo[2.2.1]heptane (II) is much lower as compared to e.g. phenols which makes them less suitable for nucleophilic displacement reactions. In this regard, the higher steric hindrance of the secondary alcohol (II) as compared to phenols must also be considered which usually makes them less accessible to the benzylation reaction with a given electrophile.

Moreover, it is particularly surprising that the process of this invention can effectively be conducted in non-polar solvents such as aliphatic and aromatic hydrocarbons, e.g. n-heptane or toluene. Since ion-pairing tends to reduce the nucleophilicity of an ion, only solvents with relatively high dielectric constants such as dipolar aprotic solvents (e.g. dimethylformamide) have so far been considered as suitable for nucleophilic replacement reactions which involve the use of cesium salts (e.g. cesium carbonate) as catalyst.

The process of this invention offers several further advantages over the prior art methods including: (1) Agglomeration of salts and heavy deposit on the inner walls and various other parts of the reactor such as e.g. baffles or agitator (herein also referred to as "fouling") can be avoided which would otherwise decrease the rate of conversion and lead to major difficulties on a large scale. For example, severe agglomeration of salts building up on the inner walls and other parts of the reactor may impede proper heat transfer, heat removal and agitation in the reactor. Such reactor fouling virtually does not occur in the process of this invention because salts formed during the reaction are suspended in the reaction medium as finely divided particles. (2) The inert organic solvent S1 used in this invention can be recovered and recycled easily which leads to an economical and sustainable process. (3) Side-product formation can be avoided. (4) Higher yields of the desired (±)-2-exo-(2-Methylbenzyloxy)-1-methyl-4-isopropyl-7-oxabicyclo[2.2.1]heptane of the formula (I), any of its individual enantiomers or any non-racemic mixture thereof can be obtained which implies higher space-time yields due to the catalytic effect of the rubidium and/or cesium salt.

Thus, the process of this invention allows the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof to proceed in a smooth and controlled manner, which is very safe, industrially simple, economical, environmentally friendly and commercially viable.

Further embodiments of the invention are evident from the claims, the description and the examples. It is to be understood that the single features of the subject matter of the invention described herein can be applied not only in the combination given in each particular case but also in other combinations, without leaving the scope of the invention.

The starting materials according to the present invention are known compounds that are commercially available or can be prepared in a known manner.

For example, (±)-2-exo-hydroxy-1-methyl-4-isopropyl-7-oxabicyclo[2.2.1]heptane of the formula (II), any of its individual enantiomers or any non-racemic mixture thereof can be prepared by any of the methods described in EP 0 081 893 A2 (see Example 15), U.S. Pat. No. 4,487,945 (see Embodiments 1 and 45), U.S. Pat. No. 4,542,244 (see Embodiments 1 and 217) and U.S. Pat. No. 4,670,041 (see Embodiments 1 and 217) or in an analogous manner.

In the 2-Methylbenzyl compound of the formula (III), the substituent X is a leaving group. The term "leaving group" as used herein refers to any group that departs the molecule with a pair of electrons in heterolytic bond cleavage such that the molecule is capable of participating in the nucleophilic substitution reaction with (±)-2-exo-hydroxy-1-methyl-4-isopropyl-7-oxabicyclo[2.2.1]heptane (II), any of its individual enantiomers or any non-racemic mixture thereof.

Preferred leaving groups X are selected from halogen, an oxygen linked leaving group, an ammonium group of the formula (IV)

$$-N(R_1)(R_2)(R_3)^+Y^-$$ (IV)

wherein $R_1$, $R_2$ and $R_3$ are each independently selected from $C_1$-$C_6$-alkyl, $C_3$-$C_{10}$-cycloalkyl and $C_6$-$C_{20}$-aryl, and $Y^-$ is selected from halide, hydroxide, $C_1$-$C_4$-alkyl sultanate and $C_6$-$C_{20}$-aryl sulfonate ions.

The organic moieties mentioned in the definition of certain variables (i.e. $R^1$, $R^2$ and $R^3$), sulfonates (i.e. $C_1$-$C_4$-alkyl sultanates, $C_1$-$C_4$-haloalkyl sulfonates, $C_6$-$C_{20}$-aryl sultanates and $C_3$-$C_{10}$-cycloalkyl sultanates) and phase transfer catalysts (i.e. tetra-n-$C_1$-$C_4$-alkyl-ammonium chlorides, bromides, iodides or hydroxides, tetra-n-$C_1$-$C_8$-alkylammonium chlorides, bromides, iodides or hydroxides and tetra-n-$C_1$-$C_{12}$-alkyl-ammonium chlorides, bromides, iodides or hydroxides) are—like the term halogen—collective terms for individual enumerations of the individual group members. The term "halogen" denotes in each case fluorine, chlorine, bromine or iodine. All hydrocarbon chains, e.g. alkyl chains, can be straight-chain or branched, the prefix $C_n$-$C_m$ denoting in each case the possible number of carbon atoms in the group. Examples of such meanings are:

$C_1$-$C_4$-alkyl: for example methyl, ethyl, n-propyl, isopropyl (—CH(CH$_3$)$_2$), n-butyl, sec-butyl (—CH(CH$_3$)—C$_2$H$_5$), isobutyl (—CH$_2$—CH(CH$_3$)$_2$) or tert-butyl (—C(CH$_3$)$_3$);

—$C_1$-$C_6$-alkyl: $C_1$-$C_4$-alkyl as mentioned above, and also, for example, n-pentyl, 1-methyl-butyl, 2-methylbutyl, 3-methylbutyl, 2,2-dimethylpropyl, 1-ethylpropyl, n-hexyl, 1,1-dimethylpropyl, 1,2-dimethylpropyl, 1-methyl pentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

$C_1$-$C_8$-alkyl: $C_1$-$C_6$-alkyl as mentioned above, and also, for example, n-heptyl, n-octyl or 2-ethylhexyl;

$C_1$-$C_{12}$-alkyl: $C_1$-$C_8$-alkyl as mentioned above, and also, for example, n-nonyl, iso-nonyl, n-decyl, n-undecyl or n-dodecyl;

$C_1$-$C_4$-haloalkyl: a $C_1$-$C_4$-alkyl as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichloro-fluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl or 1-trifluoromethyl-1,2,2,2-tetrafluoroethyl; and $C_3$-$C_{10}$-cycloalkyl: for example cyclopropyl, cyclobutyl, cyclopentyl, cyclohexyl, cycloheptyl, cyclooctyl, cyclononyl or cyclodecyl.

The term "$C_6$-$C_{20}$-aryl" as used herein refers to an unsaturated aromatic carbocyclic group of from 6 to 20 carbon atoms having a single ring (e.g., phenyl) or multiple condensed (fused) rings, wherein at least one ring is aromatic (e.g. naphthalenyl or dihydrophenanthrenyl). Examples of $C_6$-$C_{20}$-aryls include phenyl, p-toluenyl, 1-naphthalenyl (1-naphthyl), 2-naphthalenyl (2-naphthyl), anthracenyl, indenyl or phenanthrenyl. A preferred aryl group is phenyl.

The term "halide ion" as used herein refers to e.g. a fluoride ion, a chloride ion, a bromide ion or an iodide ion.

Preferred oxygen linked leaving groups are selected from $C_1$-$C_4$-alkyl sulfonates, $C_1$-$C_4$-haloalkyl sulfonates, $C_6$-$C_{20}$-aryl sulfonates, $C_3$-$C_{10}$-cycloalkyl sulfonates and imidazolylsulfonate (imidazylate), more preferably from $C_1$-$C_4$-alkyl sulfonates, $C_1$-$C_4$-haloalkyl sulfonates and $C_6$-$C_{20}$-aryl sulfonates and even more preferably from $C_1$-$C_4$-alkyl sulfonates and $C_6$-$C_{20}$-aryl sulfonates.

Examples of $C_1$-$C_4$-alkyl sulfonates include but are not limited to mesylate (methanesulfonate), esylate (ethanesulfonate), n-propylsulfonate, iso-propylsulfonate, n-butylsulfonate, iso-butyl-sulfonate, sec-butylsulfonate and tert-butylsulfonate.

Examples of $C_1$-$C_4$-haloalkyl sulfonates include but are not limited to triflate (trifluoromethanesulfonate) and trichloromethanesulfonate.

Examples of $C_6$-$C_{20}$-aryl sulfonates include but are not limited to tosylate (p-toluenesulfonate), besylate (benzenesulfonate) and 2-naphtyl sulfonate.

Examples of $C_3$-$C_{10}$-cycloalkyl sultanates include but are not limited to cyclohexylsulfonate.

Preferably, the oxygen linked leaving group is selected from mesylate (methanesulfonate), esylate (ethanesulfonate), n-propylsulfonate, iso-propylsulfonate, n-butylsulfonate, iso-butyl-sulfonate, sec-butylsulfonate, tert-butylsulfonate, triflate (trifluoromethanesulfonate), trichloromethanesulfonate, tosylate (p-toluenesulfonate), besylate (benzenesulfonate), 2-naphtyl sulfonate, cyclohexylsulfonate and imidazolylsulfonate (imidazylate), more preferably from mesylate, esylate, triflate, tosylate and besylate and even more preferably from mesylate and tosylate.

In another preferred embodiment, the leaving group X is selected from halogen, a $C_1$-$C_4$-alkyl sulfonate, a $C_6$-$C_{20}$-aryl sulfonate and an ammonium group of the formula (IV)

$$—N(R_1)(R_2)(R_3)^+Y— \qquad (IV)$$

wherein $R_1$, $R_2$ and $R_3$ are each independently selected from $C_1$-$C_6$-alkyl and $Y^-$ is selected from halide, hydroxide, $C_1$-$C_4$-alkyl sulfonate and $C_6$-$C_{20}$-aryl sulfonate ions.

More preferably, the leaving group X is selected from halogen, a $C_1$-$C_4$-alkyl sultanate, a $C_6$-$C_{20}$-aryl sultanate and an ammonium group of the formula (IV) wherein $R_1$, $R_2$ and $R_3$ are each independently selected from $C_1$-$C_6$-alkyl and $Y^-$ is selected from a halide, hydroxide, mesylate and tosylate ion.

Even more preferably, the leaving group X is selected from halogen, a $C_1$-$C_4$-alkyl sulfonate, a $C_6$-$C_{20}$-aryl sulfonate and an ammonium group of the formula (IV) wherein $R_1$, $R_2$ and $R_3$ are each independently selected from $C_1$-$C_6$-alkyl and $Y^-$ is selected from a halide ion (preferably a chloride ion).

Still more preferably, the leaving group X is selected from chlorine, bromine, iodine, mesylate, tosylate, a trimethyl ammonium chloride group of the formula (IVa)

$$—N(CH_3)_3^+Cl^-, \text{ and} \qquad (IVa)$$

a triethyl ammonium chloride group of the formula (IVb)

$$—N(CH_2CH_3)_3^+Cl^- \qquad (IVb).$$

Yet more preferably, the leaving group X is selected from chlorine, bromine, iodine, mesylate, tosylate and a trimethyl ammonium chloride group of the formula (IVa).

Still even more preferably, the leaving group X is selected from chlorine, mesylate, tosylate and a trimethyl ammonium chloride group of the formula (IVa).

In another preferred embodiment, the leaving group X is selected from halogen, in particular from chlorine, bromine and iodine. Most preferably, the leaving group X is chlorine.

In yet another embodiment, the 2-Methylbenzyl compound of the formula (III) is selected from the group consisting of 2-Methylbenzyl chloride (1-(chloromethyl)-2-methylbenzene) of the formula (IIIa)

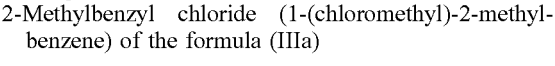

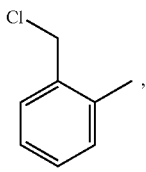
(IIIa)

2-Methylbenzyl bromide (1-(bromomethyl)-2-methyl-benzene) of the formula (IIIb)

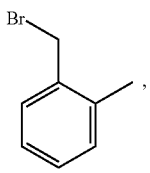
(IIIb)

2-Methylbenzyl iodide (1-(iodomethyl)-2-methyl-benzene) of the formula (IIIc)

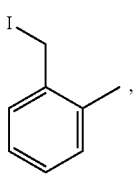
(IIIc)

2-Methylbenzyl mesylate ((2-Methylphenyl)methyl methanesulfonate) of the formula (IIId)

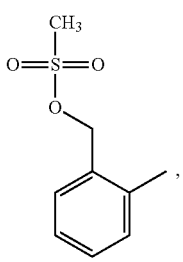
(IIId)

2-Methylbenzyl tosylate ((2-methylphenyl)methyl 4-methylbenzenesulfonate) of the formula (IIIe)

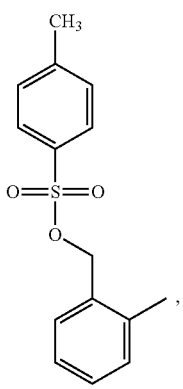
(IIIe)

Trimethyl(o-tolylmethyl)ammonium chloride of the formula (IIIf)

(IIIf)

and
Triethyl(o-tolylmethyl)ammonium chloride of the formula (IIIg)

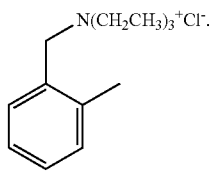
(IIIg)

Most preferably, the 2-Methylbenzyl compound of the formula (III) is 2-Methylbenzyl chloride (1-(chloromethyl)-2-methyl-benzene) of the formula (IIIa).

The 2-Methylbenzyl compound of the formula (III) used as a starting material in the process of this invention is either commercially available or can be prepared by methods known in the art or in an analogous manner.

For example, a 2-Methylbenzyl compound of the formula (III) wherein X is halogen (such as e.g. 2-Methylbenzyl chloride of the formula (IIIa)) may be prepared by the method described in Synthetic Communications, Volume 33, Issue 7, pages 1103-1107, 2003 or in an analogous manner.

For example, the 2-Methylbenzyl compound of the formula (III) wherein X is a $C_1$-$C_4$-alkyl sulfonate or $C_6$-$C_{20}$-aryl sulfonate (such as e.g. 2-Methylbenzyl mesylate of the formula (IIId) or 2-Methylbenzyl tosylate of the formula (IIIe)) may be prepared by methods described in Energy & Fuels, 21(3), pages 1695-1698, 2007 or Phosphorus, Sulfur and Silicon and the Related Elements, 184(5), pages 1161-1174, 2009.

The 2-Methylbenzyl compound of the formula (III) wherein X is an ammonium group of the formula (IV) (such as e.g. trimethyl(o-tolylmethyl)ammonium chloride of the formula (IIIf) or triethyl(o-tolylmethyl)ammonium chloride of the formula (IIIg)) may be prepared by methods analogous to those described in Organic Syntheses, Coll. Vol. 4, p.98 (1963); Vol. 38, p. 5 (1958). For example, the 2-Methylbenzyl compound of the formula (III) wherein X is selected from halogen (preferably chlorine, bromine or iodine and more preferably chlorine), a $C_1$-$C_4$-alkyl sulfonate (preferably mesylate) or a $C_6$-$C_{20}$-aryl sulfonate (preferably tosylate) is reacted with a tertiary amine of the formula $NR_1R_2R_3$ wherein $R_1$, $R_2$ and $R_3$ have the same meaning as in formula (IV) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl) in a suitable solvent such as e.g. anhydrous ethanol.

The 2-Methylbenzyl compound of the formula (III) wherein X is an ammonium group of the formula (IV) (such as e.g. trimethyl(o-tolylmethyl)ammonium chloride of the formula (IIIf) or triethyl(o-tolylmethyl)ammonium chloride of the formula (IIIg)) can be added to the reaction mixture separately (i.e. as isolated substance or in solution of any suitable solvent), or formed in the reaction mixture in-situ.

When the in-situ formation of the 2-Methylbenzyl compound of the formula (III) wherein X is an ammonium group of the formula (IV) (such as e.g. trimethyl(o-tolylmethyl) ammonium chloride of the formula (IIIf) or triethyl(o-tolylmethyl)ammonium chloride of the formula (IIIg)) is desired, the process of this invention is conducted in the presence of at least one tertiary amine of the formula $NR_1R_2R_3$ wherein $R_1$, $R_2$ and $R_3$ have the same meaning as in formula (IV) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl).

Examples of suitable tertiary amines of the formula $NR_1R_2R_3$ are tri-($C_1$-$C_6$)-alkylamines such as trimethylamine, triethylamine, tributylamine and N,N-diisopropylethylamine; di-($C_1$-$C_6$)-alkyl-phenylamines such as N,N-dimethylaniline and N,N-diethylaniline; and the like.

Preferably, a tertiary amine of the formula $NR_1R_2R_3$ is used wherein $R_1$, $R_2$ and $R_3$ are each $C_1$-$C_6$-alkyl, more preferably $C_1$-$C_4$-alkyl, in particular methyl or ethyl and most preferably methyl.

Thus, in an especially preferred embodiment, the tertiary amine of the formula $NR_1R_2R_3$ is selected from trimethylamine, triethylamine or a combination thereof. Most preferably, the tertiary amine of the formula $NR_1R_2R_3$ is trimethylamine.

In particular, the 2-Methylbenzyl compound of the formula (III) wherein X is an ammonium group of the formula (IV) (such as e.g. trimethyl(o-tolylmethyl)ammonium chloride of the formula (IIIf) or triethyl(o-tolylmethyl)ammonium chloride of the formula (IIIg)) may be formed in-situ by reacting the 2-Methylbenzyl compound of the formula (III) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) with a tertiary amine of the formula $NR_1R_2R_3$ wherein $R_1$, $R_2$ and $R_3$ have the same meaning as in formula (IV) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl) in the reaction mixture comprising (±)-2-exo-hydroxy-1-methyl-4-isopropyl-7-oxabicyclo[2.2.1]heptane of the formula (II), any of its individual enantiomers or any non-racemic mixture thereof, the base as defined herein, the catalyst as defined herein and the inert organic solvent S1 as defined herein.

More specifically, the in-situ formation of the 2-Methylbenzyl compound of the formula (III) wherein X is an ammonium group of the formula (IV) (such as e.g. trimethyl(o-tolylmethyl)ammonium chloride of the formula (IIIf) or triethyl(o-tolylmethyl)ammonium chloride of the formula (IIIg)) can be accomplished by placing (±)-2-exo-hydroxy-1-methyl-4-isopropyl-7-oxabicyclo[2.2.1]heptane of the formula (II), any of its individual enantiomers or any non-racemic mixture thereof, the base as defined herein, the catalyst as defined herein, the inert organic solvent S1 as defined herein and the tertiary amine of the formula $NR_1R_2R_3$ as defined herein into a reactor to give a first mixture, heating said first mixture, metering the 2-Methylbenzyl compound of the formula (III) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) into the first mixture to give the reaction mixture.

It is envisioned that the tertiary amine $NR_1R_2R_3$ replaces the leaving group X in the 2-Methylbenzyl compound of the formula (III) wherein X is selected from halogen, a $C_1$-$C_4$-alkyl sulfonate or a $C_6$-$C_{20}$-aryl sultanate (preferably halogen, more preferably chlorine, bromine or iodine and even more preferably chlorine) to form the respective ammonium-salt, i.e. the 2-Methylbenzyl compound of the formula (III) wherein X is an ammonium group of the formula (IV) (such as e.g. trimethyl(o-tolylmethyl)ammonium chloride of the formula (IIIf) or triethyl(o-tolylmethyl)ammonium chloride of the formula (IIIg)). The ammomium salt formed in-situ immediately reacts with the salt of (±)-2-exo-hydroxy-1-methyl-4-isopropyl-7-oxabicyclo[2.2.1]heptane of the formula (II), any of its individual enantiomers or any non-racemic mixture thereof being present in the reaction mixture. During this benzylation, the tertiary amine is released again and thus available for restarting the nucleophilic substitution of the 2-Methylbenzyl compound of the formula (III) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine).

The aforementioned in-situ formation of the 2-Methylbenzyl compound of the formula (III) wherein X is an ammonium group of the formula (IV) is further illustrated in the following reaction scheme.

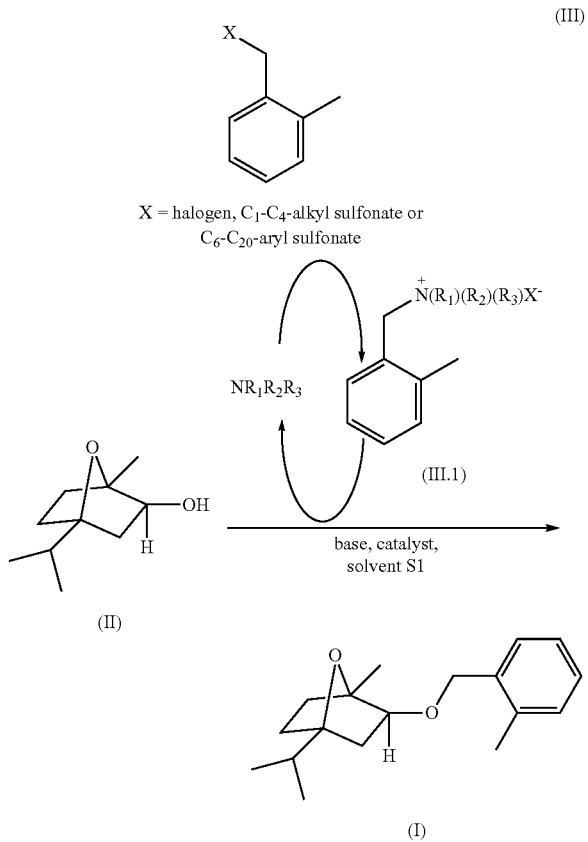

Hence, this variant of the process according to the invention is particularly advantageous because only substoichiometric or even catalytic amounts of the tertiary amine $NR_1R_2R_3$ relative to the 2-Methylbenzyl compound of the formula (III) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) are required without discontinuing the benzylation reaction. Moreover, the higher electrophilicity due to the ionic nature of the 2-Methylbenzyl compound of the formula (III) wherein X is an ammonium group of the formula (IV) leads to an acceleration of the reaction as compared to directly using the 2-Methylbenzyl compound of the formula (III) wherein X is selected from halogen, a $C_1$-$C_4$-alkyl sulfonate or a $C_6$-$C_{20}$-aryl sulfonate as the electrophilic reagent. Further, the amphiphilic character of the 2-Methylbenzyl compound of the formula (III) wherein X is an ammonium group of the formula (IV) is also beneficial given that the reaction medium forms a heterogeneous mixture comprising a liquid and solid phase.

The molar ratio of the 2-Methylbenzyl compound of the formula (III) (in particular 2-Methylbenzyl chloride of the formula (IIIa)) to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), can vary widely and depends on the nature of the 2-Methylbenzyl compound (III) employed and the reaction conditions used, but is generally from 3:1 to 0.9:1, preferably from 2:1 to 0.9:1, more preferably from 1.5:1 to 0.9:1 and even more preferably from 1.1:1 to 0.9:1.

In another embodiment, the process of this invention is conducted in the presence of at least one base capable of forming a solvent S2 selected from water, a $C_1$-$C_4$ alkyl alcohol or any combination thereof under the reaction conditions.

Examples of $C_1$-$C_4$-alkyl alcohols include methanol, ethanol, n-propanol, iso-propanol (propan-2-ol), n-butanol, sec-butanol (butan-2-ol), iso-butanol (2-methyl-1-propanol) or tert-butanol (2-methyl-2-propanol), preferably methanol, ethanol, iso-propanol or tert-butanol and more preferably methanol.

In a preferred embodiment, the process of this invention is conducted in the presence of at least one base capable of forming a solvent S2 selected from water, methanol, ethanol, iso-propanol, tert-butanol or any combination thereof (more preferably water, methanol, ethanol, tert-butanol or any combination thereof, even more preferably water, methanol or a combination thereof and in particular water) under the reaction conditions.

In particular, the base used in this invention is selected from alkali metal and alkaline earth metal hydroxides, alkali metal and alkaline earth metal carbonates, alkali metal and alkaline earth metal hydrogen carbonates, alkali metal and alkaline earth metal oxides, alkali metal and alkaline earth metal $C_1$-$C_4$ alcoholates and any combination thereof, more preferably from alkali metal and alkaline earth metal hydroxides, alkali metal and alkaline earth metal carbonates, alkali metal and alkaline earth metal $C_1$-$C_4$ alcoholates and any combination thereof, even more preferably from alkali metal hydroxides, alkali metal carbonates, alkali metal $C_1$-$C_4$ alcoholates and any combination thereof, yet more preferably from alkali metal hydroxides, alkali metal $C_1$-$C_4$ alcoholates and any combination thereof, and still more preferably from alkali metal hydroxides.

The term "alkali metal" as used herein includes e.g. lithium, sodium and potassium.

The term "alkaline earth metal" as used herein includes e.g. calcium, magnesium and barium.

In another embodiment, the base is selected from alkali metal and alkaline earth metal hydroxides, alkali metal and alkaline earth metal carbonates, alkali metal and alkaline earth metal hydrogen carbonates, alkali metal and alkaline earth metal oxides, alkali metal and alkaline earth metal $C_1$-$C_4$ alcoholates and any combination thereof, preferably from alkali metal and alkaline earth metal hydroxides, alkali metal and alkaline earth metal carbonates, alkali metal and alkaline earth metal $C_1$-$C_4$ alcoholates and any combination thereof, each alkali metal being independently selected from lithium, sodium and potassium and each alkaline earth metal being independently selected from calcium, magnesium and barium.

In yet another embodiment, the base is selected from alkali metal hydroxides, alkali metal carbonates, alkali metal hydrogen carbonates, alkali metal oxides, alkali metal $C_1$-$C_4$ alcoholates and any combination thereof, preferably from alkali metal hydroxides, alkali metal $C_1$-$C_4$ alcoholates and any combination thereof, and more preferably from alkali metal hydroxides, each alkali metal being independently selected from lithium, sodium and potassium.

As alkali metal hydroxides, there can be used lithium hydroxide, sodium hydroxide and potassium hydroxide.

As alkaline earth metal hydroxides, there can be used calcium hydroxide, magnesium hydroxide or barium hydroxide.

As alkali metal carbonates, there can be used lithium carbonate, sodium carbonate or potassium carbonate.

As alkaline earth metal carbonates, there can be used calcium carbonate, magnesium carbonate or barium carbonate.

As alkali metal hydrogen carbonates, there can be used lithium hydrogen carbonate, sodium hydrogen carbonate or potassium hydrogen carbonate.

As alkaline earth metal hydrogen carbonates, there can be used calcium hydrogen carbonate, magnesium hydrogen carbonate or barium hydrogen carbonate.

As alkali metal oxides, there can be used lithium oxide, sodium oxide or potassium oxide.

As alkaline earth metal oxides, there can be used calcium oxide, magnesium oxide or barium oxide.

As alkali metal $C_1$-$C_4$ alcoholates, there can be used lithium methoxide, sodium methoxide, potassium methoxide, lithium ethoxide, sodium ethoxide, potassium ethoxide, lithium n-propoxide, sodium n-propoxide, potassium n-propoxide, lithium iso-propoxide, sodium iso-propoxide, potassium iso-propoxide, lithium n-butoxide, sodium n-butoxide, potassium n-butoxide, lithium tert-butoxide, sodium tert-butoxide or potassium tert-butoxide.

As alkaline earth metal $C_1$-$C_4$ alcoholates, there can be used magnesium dimethoxide, calcium dimethoxide, barium dimethoxide, magnesium diethoxide, calcium diethoxide, barium diethoxide, magnesium di-n-propoxide, calcium di-n-propoxide, barium di-n-propoxide, magnesium di-iso-propoxide, calcium di-iso-propoxide, barium di-iso-propoxide, magnesium di-n-butoxide, calcium di-n-butoxide, barium di-n-butoxide, magnesium di-tert-butoxide, calcium di-tert-butoxide or barium di-tert-butoxide.

In a preferred embodiment, the base used in this invention is selected from lithium hydroxide, sodium hydroxide, potassium hydroxide, calcium hydroxide, magnesium hydroxide, barium hydroxide, lithium carbonate, sodium carbonate, potassium carbonate, calcium carbonate, magnesium carbonate, barium carbonate, lithium hydrogen carbonate, sodium hydrogen carbonate, potassium hydrogen carbonate, calcium hydrogen carbonate, magnesium hydrogen carbonate, barium hydrogen carbonate, lithium oxide, sodium oxide, potassium oxide, calcium oxide, magnesium oxide, barium oxide, lithium methoxide, sodium methoxide, potassium methoxide, lithium ethoxide, sodium ethoxide, potassium ethoxide, lithium n-propoxide, sodium n-propoxide, potassium n-propoxide, lithium iso-propoxide, sodium iso-propoxide, potassium iso-propoxide, lithium n-butoxide, sodium n-butoxide, potassium n-butoxide, lithium tert-butoxide, sodium tert-butoxide, potassium tert-butoxide, magnesium dimethoxide, calcium dimethoxide, barium di-methoxide, magnesium diethoxide, calcium diethoxide, barium diethoxide, magnesium di-n-propoxide, calcium di-n-propoxide, barium di-n-propoxide, magnesium di-iso-propoxide, calcium di-iso-propoxide, barium di-iso-propoxide, magnesium di-n-butoxide, calcium di-n-butoxide, barium di-n-butoxide, magnesium di-tert-butoxide, calcium di-tert-butoxide, barium di-tert-butoxide and any combination thereof, more preferably from lithium hydroxide, sodium hydroxide, potassium hydroxide, calcium hydroxide, magnesium hydroxide, barium hydroxide, lithium carbonate, sodium carbonate, potassium carbonate, calcium carbonate, magnesium carbonate, barium carbonate, lithium methoxide, sodium methoxide, potassium methoxide, magnesium dimethoxide, calcium dimethoxide, barium dimethoxide and any combination thereof, even more preferably from lithium hydroxide, sodium hydroxide, potassium hydroxide, lithium carbonate, sodium carbonate, potassium carbonate, lithium methoxide, sodium methoxide, potassium methoxide and any combination thereof, still more preferably from lithium hydroxide, sodium hydroxide, potassium hydroxide, lithium methoxide, sodium methoxide, potassium methoxide and any combination thereof, yet more preferably from sodium hydroxide, potassium hydroxide, sodium methoxide, potassium methoxide and any combination thereof and still even more preferably from sodium hydroxide, potassium hydroxide and a combination thereof. Most preferably, the base used in this invention is sodium hydroxide.

In another embodiment, the base is selected from lithium hydroxide, sodium hydroxide, potassium hydroxide and any combination thereof.

The molar ratio of the base to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), can vary widely and depends on the reaction conditions used, but is generally from 1:1 to 5:1, preferably from 1:1 to 3:1, more preferably from 1:1 to 2:1 and even more preferably from 1:1 to 1.5:1.

The base used in this invention can be added to the reaction mixture in solid form, as an aqueous solution or as a combination thereof.

The term "solid form" as used herein includes but is not limited to powders, tablets, pellets, flakes, granules or micropearls.

The concentration of the base in the aqueous solution can vary and depends on the nature of the base and the reaction conditions used, but is generally from 5 to 50% by weight, preferably 10 to 50% by weight and more preferably 30 to 50% by weight of the base, based on the weight of the aqueous solution.

Bases selected from alkali metal hydroxides (preferably from lithium hydroxide, sodium hydroxide, potassium hydroxide and any combination thereof, more preferably from sodium hydroxide, potassium hydroxide and a combination thereof and most preferably sodium hydroxide) are preferably added to the reaction mixture in solid form. As solid forms of alkali metal hydroxides, there can be used pellets, flakes, granules or micropearls, preferably micropearls. The aforementioned solid forms of alkali metal hydroxides are commercially available from various suppliers. In a preferred embodiment, the process of this invention is conducted in the presence of sodium hydroxide micropearls as the base. Thus, the base used in this invention preferably comprises sodium hydroxide micropearls and more preferably consists of sodium hydroxide micropearls.

In another embodiment, bases selected from alkali metal hydroxides (preferably from lithium hydroxide, sodium hydroxide, potassium hydroxide and any combination thereof, more preferably from sodium hydroxide, potassium hydroxide and a combination thereof and most preferably sodium hydroxide) may also be added to the reaction mixture as an aqueous solution. Preferably, the aqueous solution of the alkali metal hydroxide (preferably sodium hydroxide or potassium hydroxide and more preferably sodium hydroxide) comprises from 10 to 50% by weight, more preferably 25 to 50% by weight and even more preferably 35 to 50% by weight of the alkali metal hydroxide (preferably sodium hydroxide or potassium hydroxide and more preferably sodium hydroxide), based on the weight of the aqueous solution. Aqueous solutions of alkali metal hydroxides (preferably sodium hydroxide or potassium hydroxide and more preferably sodium hydroxide) can be provided by known methods but are also commercially available at a number of different concentrations.

The process of this invention is carried out in the presence of at least one catalyst selected from rubidium salts, cesium salts and any combination thereof.

In one embodiment, the catalyst is selected from rubidium salts.

In another embodiment, the catalyst is selected from cesium salts.

Preferably, the catalyst is selected from rubidium and cesium salts of inorganic acids, rubidium and cesium salts of organic acids and any combination thereof.

In one embodiment, the catalyst is selected from rubidium salts of inorganic acids, rubidium salts of organic acids and any combination thereof.

In another embodiment, the catalyst is selected from cesium salts of inorganic acids, cesium salts of organic acids and any combination thereof.

More preferably, the catalyst is selected from rubidium and cesium salts of inorganic acids.

In one embodiment, the catalyst is selected from rubidium salts of inorganic acids.

In another embodiment, the catalyst is selected from cesium salts of inorganic acids.

The term "salts of inorganic acids" as used herein includes, for example, halides, carbonates, sulfates, nitrate, phosphates, oxide and hydroxide.

The term "halides" as used herein includes fluoride, chloride, bromide and iodide.

The term "carbonates" as used herein includes, for example, carbonate ($CO_3^{2-}$) and hydrogen carbonate ($HCO_3^-$).

The term "sulfates" as used herein includes, for example, sulfate ($SO_4^{2-}$) and hydrogen sulfate ($HSO_4^-$).

The term "phosphates" as used herein includes, for example, phosphate ($PO_4^{3-}$), hydrogen phosphate ($HPO_4^{2-}$) and dihydrogen phosphate ($H_2PO_4^-$).

The term "salts of organic acids" as used herein includes, for example, carboxylates, alcoholates and sulfonates.

The term "carboxylates" as used herein includes, for example, formates, acetates, oxalates, lactates and citrates.

The term "alcoholates" as used herein in the definition of the catalyst includes, for example, $C_1$-$C_4$ alcoholates such as methoxide, ethoxide, n-propoxide, iso-propoxide, n-butoxide, sec-butoxide and tert-butoxide.

The term "sulfonates" as used herein in the definition of the catalyst includes, for example, $C_1$-$C_4$-alkyl sulfonates such as mesylate (methanesulfonate), esylate (ethanesulfonate), n-propylsulfonate, iso-propylsulfonate, n-butylsulfonate, iso-butylsulfonate, sec-butylsulfonate and tert-butylsulfonate, $C_1$-$C_4$-haloalkyl sulfonates such as triflate (trifluoromethanesulfonate) and trichloromethanesulfonate and $C_6$-$C_{20}$-aryl sulfonates such as tosylate (para-toluenesulfonate), besylate (benzenesulfonate) and 2-naphtyl sulfonate, in particular methanesulfonate, trifluoro-methanesulfonate and para-toluenesufonate.

In another preferred embodiment, the catalyst is selected from rubidium and cesium halides, rubidium and cesium carbonates, rubidium and cesium sulfates, rubidium and cesium nitrate, rubidium and cesium phosphates, rubidium and cesium oxide, rubidium and cesium hydroxide, rubidium and cesium carboxylates, rubidium and cesium $C_1$-$C_4$ alcoholates, rubidium and cesium sulfonates and any combination thereof, more preferably from rubidium and cesium halides, rubidium and cesium carbonates, rubidium and cesium sulfates, rubidium and cesium hydroxide and any combination thereof, even more preferably from rubidium and cesium halides, rubidium and cesium carbonates, rubidium and cesium hydroxide and any combination thereof, yet more preferably from rubidium and cesium halides, rubidium and cesium carbonates and any combination thereof and in particular from rubidium and cesium halides.

In one embodiment, the catalyst is selected from the catalyst is selected from rubidium halides, rubidium carbonates, rubidium sulfates, rubidium nitrate, rubidium phosphates, rubidium oxide, rubidium hydroxide, rubidium carboxylates, rubidium $C_1$-$C_4$ alcoholates, rubidium sulfonates and any combination thereof, more preferably from rubidium halides, rubidium carbonates, rubidium sulfates, rubidium hydroxide and any combination thereof, even more preferably from rubidium halides, rubidium carbonates, rubidium hydroxide and any combination thereof, yet more preferably from rubidium halides, rubidium carbonates and any combination thereof and in particular from rubidium halides.

In another embodiment, the catalyst is selected from cesium halides, cesium carbonates, cesium sulfates, cesium nitrate, cesium phosphates, cesium oxide, cesium hydroxide, cesium carboxylates, cesium $C_1$-$C_4$ alcoholates, cesium sulfonates and any combination thereof, more preferably from cesium halides, cesium carbonates, cesium sulfates, cesium hydroxide and any combination thereof, even more preferably from cesium halides, cesium carbonates, cesium hydroxide and any combination thereof, yet more preferably from cesium halides, cesium carbonates and any combination thereof and in particular from cesium halides.

In a more preferred embodiment, the catalyst is selected from rubidium fluoride, rubidium chloride, rubidium bromide, rubidium iodide, cesium fluoride, cesium chloride, cesium bromide, cesium iodide, rubidium carbonate, rubidium hydrogen carbonate, cesium carbonate, cesium hydrogen carbonate, rubidium sulfate, rubidium hydrogen sulfate, cesium sulfate, cesium hydrogen sulfate, rubidium nitrate, cesium nitrate, rubidium phosphate, rubidium hydrogen phosphate, rubidium dihydrogen phosphate, cesium phosphate, cesium hydrogen phosphate, cesium dihydrogen phosphate, rubidium oxide, cesium oxide, rubidium hydroxide, cesium hydroxide, rubidium formate, rubidium acetate, rubidium oxalate, rubidium lactate, rubidium citrate, cesium formate, cesium acetate, cesium oxalate, cesium lactate, cesium citrate, rubidium methoxide, rubidium ethoxide, rubidium n-propoxide, rubidium iso-propoxide, rubidium n-butoxide, rubidium sec-butoxide, rubidium tert-butoxide, cesium methoxide, cesium ethoxide, cesium n-propoxide, cesium iso-propoxide, cesium n-butoxide, cesium sec-butoxide, cesium tert-butoxide, rubidium methanesulfonate, rubidium trifluoromethanesulfonate, rubidium para-toluenesufonate, cesium methanesulfonate, cesium trifluoromethanesulfonate, cesium para-toluenesufonate and any combination thereof, more preferably from rubidium fluoride, rubidium chloride, rubidium bromide, rubidium iodide, cesium fluoride, cesium chloride, cesium bromide, cesium iodide, rubidium carbonate, cesium carbonate, rubidium sulfate, cesium sulfate, rubidium phosphate, cesium phosphate, rubidium hydroxide, cesium hydroxide and any combination thereof, even more preferably from rubidium chloride, cesium chloride, rubidium carbonate, cesium carbonate, rubidium sulfate, cesium sulfate, rubidium hydroxide, cesium hydroxide and any combination thereof, yet more preferably from rubidium chloride, cesium chloride, rubidium carbonate, cesium carbonate, rubidium hydroxide, cesium hydroxide and any combination thereof, still more preferably from rubidium chloride, cesium chloride, rubidium carbonate, cesium carbonate and any combination thereof and in particular from rubidium chloride, cesium chloride or a combination thereof.

In one embodiment, the catalyst is selected from rubidium fluoride, rubidium chloride, rubidium bromide, rubidium iodide, rubidium carbonate, rubidium hydrogen carbonate, rubidium sulfate, rubidium hydrogen sulfate, rubidium nitrate, rubidium phosphate, rubidium hydrogen phosphate, rubidium dihydrogen phosphate, rubidium oxide, rubidium hydroxide, rubidium formate, rubidium acetate, rubidium oxalate, rubidium lactate, rubidium citrate, rubidium methoxide, rubidium ethoxide, rubidium n-propoxide, rubidium iso-propoxide, rubidium n-butoxide, rubidium sec-butoxide, rubidium tert-butoxide, rubidium methanesulfonate, rubidium trifluoromethanesulfonate, rubidium para-toluenesufonate and any combination thereof, more preferably from rubidium fluoride, rubidium chloride, rubidium bromide, rubidium iodide, rubidium carbonate, rubidium sulfate, rubidium phosphate, rubidium hydroxide and any combination thereof, even more preferably from rubidium chloride, rubidium carbonate, rubidium sulfate, rubidium hydroxide and any combination thereof, yet more preferably from rubidium chloride, rubidium carbonate, rubidium hydroxide and any combination thereof, still more preferably from rubidium chloride, rubidium carbonate or a combination thereof and in particular rubidium chloride.

In another embodiment, the catalyst is selected from cesium fluoride, cesium chloride, cesium bromide, cesium iodide, cesium carbonate, cesium hydrogen carbonate, cesium sulfate, cesium hydrogen sulfate, cesium nitrate, cesium phosphate, cesium hydrogen phosphate, cesium dihydrogen phosphate, cesium oxide, cesium hydroxide, cesium formate, cesium acetate, cesium oxalate, cesium lactate, cesium citrate, cesium methoxide, cesium ethoxide, cesium n-propoxide, cesium iso-propoxide, cesium n-butoxide, cesium sec-butoxide, cesium tert-butoxide, cesium methanesulfonate, cesium trifluoromethanesulfonate, cesium para-toluenesufonate and any combination thereof, more preferably from cesium fluoride, cesium chloride, cesium bromide, cesium iodide, cesium carbonate, cesium sulfate, cesium phosphate, cesium hydroxide and any combination thereof, even more preferably from cesium chloride, cesium carbonate, cesium sulfate, cesium hydroxide and any combination thereof, yet more preferably from cesium chloride, cesium carbonate, cesium hydroxide and any combination thereof, still more preferably from cesium chloride, cesium carbonate or a combination thereof and in particular cesium chloride.

The catalyst is preferably added to the reaction mixture in solid form but can also be added as a solution in an appropriate solvent. The catalyst may also be supported on a support material.

Preferably, the molar ratio of the catalyst to (±)-2-exo-hydroxy-1-methyl-4-isopropyl-7-oxabicyclo[2.2.1]heptane of the formula (II) is from 0.001:1 to 0.5:1, more preferably from 0.005:1 to 0.3:1, even more preferably from 0.0075:1 to 0.2:1, yet more preferably from 0.01:1 to 0.1:1 and in particular from 0.0125:1 to 0.04:1.

The process of this invention is carried out in the presence of at least one inert organic solvent S1.

By "inert organic solvent" is meant an organic solvent which, under the reaction conditions of the process of this invention, does not enter into any appreciable reaction with either the reactants or the products.

The inert organic solvent S1 used in the process of this invention can be selected from a wide variety of solvents depending upon the reaction conditions used.

Suitable inert organic solvents S1 can be selected from hydrocarbons, amides, ethers, ketones, nitriles and any combination thereof.

The hydrocarbon used as the inert organic solvent S1 in this invention may be selected from aliphatic hydrocarbons, cycloaliphatic hydrocarbons, aromatic hydrocarbons, halogenated aliphatic hydrocarbons, halogenated aromatic hydrocarbons and any combination thereof.

Preferably, the inert organic solvents S1 can be selected from aliphatic hydrocarbons, cycloaliphatic hydrocarbons, aromatic hydrocarbons, halogenated aliphatic hydrocarbons, halogenated aromatic hydrocarbons, amides, ethers, ketones, nitriles and any combination thereof.

The term "aliphatic hydrocarbons" includes straight and branched chain aliphatic hydrocarbons.

Straight chain aliphatic hydrocarbons that can be used in the present invention are those having from 5 to 15 carbon atoms, preferably 5 to 10 carbon atoms. Examples of straight chain aliphatic hydrocarbons include n-pentane, n-hexane, n-heptane, n-octane, n-nonane, n-decane or any combination thereof, preferably n-heptane, n-octane, n-nonane, n-decane or any combination thereof.

The branched chain aliphatic hydrocarbons which are suitable for use in the present invention are those having from 4 to 15 carbon atoms, preferably 5 to 12 carbon atoms, more preferably 7 to 12 carbon atoms and even more preferably 8 to 11 carbon atoms. Examples of suitable branched chain aliphatic hydrocarbons include 2-methylpropane, 2-methylbutane, 2,3-dimethyl-butane, 2-methylpentane, 3-methylpentane, 2,2-dimethylpentane, 2,3-dimethylpentane, 2,4-di-methylpentane, 2,2,4-trimethylpentane, 2-methylhexane, 3-methylhexane, 2,4-dimethylhexane, 2,5-dimethylhexane, 2,2,4-trimethylhexane, 2,3,4-trimethylhexane, 3,3,4-trimethylhexane, 2-methylheptane, 3-methylheptane, 2,3-dimethylheptane, 3,4-dimethylpentane, 2-ethyloctane, 2,3-dimethyloctane, 2-methylnonane, 3,4-dimethylnonane, 3-methyldecane, 2-methylundecane, 2-methyldodecane, 2,2,4 trimethyldodecane and any combination thereof.

Especially suitable are mixtures of branched chain aliphatic hydrocarbons having from 5 to 12 carbon atoms, preferably 7 to 12 carbon atoms and more preferably 8 to 11 carbon atoms, such as the commercial mixtures of isoparaffinic hydrocarbons sold under the tradename Isopar® by ExxonMobil Chemical, such as for example Isopar® E. Isopar E is a mixture of isoparaffinic hydrocarbons with a distillation range of 113° C. to 139° C.

Examples of suitable cycloaliphatic hydrocarbons include saturated or unsaturated cycloaliphatic hydrocarbons, such as e.g. cyclopentane, cyclohexane, cyclohexene, cycloheptane, cyclooctane, cyclooctene, 1,5-cyclooctadiene and the like. Preference is given to saturated cycloaliphatic hydrocarbons having from 5 to 10 carbon atoms. Cyclohexane is particularly preferred.

Examples of suitable aromatic hydrocarbons include toluene, o-xylene, m-xylene, p-xylene, ethylbenzene, 2-propylbenzene (cumene), 2-isopropyltoluene (o-cymol), 3-isopropyltoluene (m-cymol), 4-isopropyltoluene (p-cymol), 1,3,5-trimethylbenzene (mesitylene) and the like. Preference is given to toluene, o-xylene, m-xylene, p-xylene, ethylbenzene, 1,3,5-trimethylbenzene (mesitylene) and any combination thereof. Especially preferred among the aromatic hydrocarbons are toluene, o-xylene, m-xylene, p-xylene, 1,3,5-trimethylbenzene (mesitylene) and any combination thereof, with toluene being the most preferred.

Examples of suitable halogenated aliphatic hydrocarbons include methylene chloride, chloroform, carbon tetrachloride, 1,2-dichloroethane, 1,1,1,2-tetrachloroethane, 1,1,2,2-tetrachloroethane, 1,1-dichloroethylene, 1,2-dichloroethylene, and the like. Preference is given to methylene chloride and 1,2-dichloroethane and any combination thereof.

Examples of suitable halogenated aromatic hydrocarbons include chlorobenzene, bromobenzene, o-dichlorobenzene, m-dichlorobenzene, α,α,α-trifluorotoluene (benzotrifluoride) and the like.

Examples of suitable amides include N,N-dimethylformamide, dimethylacetamide, diethylacetamide, and the like.

Examples of suitable ethers include acyclic, cyclic or aromatic ethers such as diethyl ether, diisopropyl ether, n-butyl methyl ether, isobutyl methyl ether, sec-butyl methyl ether, tert-butyl methyl ether, cyclopentyl methyl ether, tetrahydrofuran, 2-methyltetrahydrofuran, 1,4-dioxane, anisole and the like.

Examples of suitable ketones include acetone, methyl ethyl ketone, methyl isopropyl ketone, methyl isobutyl ketone, cyclopropyl methyl ketone and the like.

Examples of suitable nitriles include acetonitrile, benzonitrile, and the like.

In a preferred embodiment, the inert organic solvent S1 is selected from hydrocarbons, acyclic ethers, cyclic ethers, aromatic ethers and any combination thereof, more preferably from aliphatic hydrocarbons, cycloaliphatic hydrocarbons, aromatic hydrocarbons, halogenated aliphatic hydrocarbons, halogenated aromatic hydrocarbons, acyclic ethers, cyclic ethers, aromatic ethers and any combination thereof, even more preferably from aliphatic hydrocarbons, aromatic hydrocarbons, halogenated aliphatic hydrocarbons, halogenated aromatic hydrocarbons and any combination thereof, yet more preferably from aliphatic hydrocarbons, aromatic hydrocarbons and any combination thereof, and still more preferably from aromatic hydrocarbons.

In another preferred embodiment, the inert organic solvent S1 is selected from hydrocarbons.

In a more preferred preferred embodiment, the inert organic solvent S1 is selected from n-heptane, n-octane, n-nonane, n-decane, toluene, o-xylene, m-xylene, p-xylene, ethylbenzene, 1,3,5-trimethylbenzene (mesitylene), methylene chloride, chlorobenzene and any combination thereof.

In an even more preferred embodiment, the inert organic solvent S1 is selected from n-heptane, n-octane, toluene, o-xylene, m-xylene, p-xylene, ethylbenzene, 1,3,5-trimethylbenzene (mesitylene), chlorobenzene, and any combination thereof.

Yet more preferably, the inert organic solvent S1 is selected from n-heptane, n-octane, toluene, o-xylene, m-xylene, p-xylene, ethylbenzene, 1,3,5-trimethylbenzene (mesitylene) and any combination thereof.

Still more preferably, the inert organic solvent S1 is selected from n-heptane, toluene, o-xylene, m-xylene, p-xylene and any combination thereof.

Particularly preferred inert organic solvents S1 are alkylbenzenes which are mono-, di-, or tri-alkyl substituted with each alkyl group containing 1 to 3 carbon atoms, in particular those selected from toluene, o-xylene, m-xylene, p-xylene, ethylbenzene, 1,3,5-trimethylbenzene (mesitylene) and any combination thereof and still more preferably selected from toluene, o-xylene, m-xylene, p-xylene and any combination thereof. Most preferably, the inert organic solvent S1 is toluene.

In another embodiment, the inert organic solvent S1 is selected from non-polar solvents and preferably from non-polar solvents having a dielectric constant of less than 15 (preferably less than 10, more preferably less than 5 and in particular less than 3) at 25° C.

In another embodiment, the catalyst is selected from rubidium and cesium halides, rubidium and cesium carbonates, rubidium and cesium hydroxide and any combination thereof (preferably from rubidium and cesium halides, rubidium and cesium carbonates and any combination thereof and in particular from rubidium and cesium halides) and the inert organic solvent S1 is selected from non-polar solvents (preferably from non-polar solvents having a dielectric constant of less than 15, more preferably less than 10, even more preferably less than 5 and in particular less than 3 at 25° C.).

In another embodiment, the catalyst is selected from rubidium halides, rubidium carbonates, rubidium and rubidium hydroxide and any combination thereof (preferably from rubidium halides, rubidium carbonates and any combination thereof and in particular from rubidium halides) and the inert organic solvent S1 is selected from non-polar solvents (preferably from non-polar solvents having a dielectric constant of less than 15, more preferably less than 10, even more preferably less than 5 and in particular less than 3 at 25° C.).

In another embodiment, the catalyst is selected from cesium halides, cesium carbonates, rubidium and cesium hydroxide and any combination thereof (preferably from cesium halides, cesium carbonates and any combination thereof and in particular from cesium halides) and the inert organic solvent S1 is selected from non-polar solvents (preferably from non-polar solvents having a dielectric constant of less than 15, more preferably less than 10, even more preferably less than 5 and in particular less than 3 at 25° C.).

In another embodiment, the catalyst is selected from rubidium and cesium halides, rubidium and cesium carbonates, rubidium and cesium hydroxide and any combination thereof (preferably from rubidium and cesium halides, rubidium and cesium carbonates and any combination thereof and in particular from rubidium and cesium halides) and the inert organic solvent S1 is selected from aliphatic hydrocarbons, aromatic hydrocarbons, halogenated aliphatic hydrocarbons, halogenated aromatic hydrocarbons and any combination thereof (preferably from aliphatic hydrocarbons, aromatic hydrocarbons and any combination thereof and more preferably from aromatic hydrocarbons).

In another embodiment, the catalyst is selected from rubidium halides, rubidium carbonates and rubidium hydroxide and any combination thereof (preferably from rubidium halides, rubidium carbonates and any combination thereof and in particular from rubidium halides) and the inert organic solvent S1 is selected from aliphatic hydrocarbons, aromatic hydrocarbons, halogenated aliphatic hydrocarbons, halogenated aromatic hydrocarbons and any combination thereof (preferably from aliphatic hydrocarbons, aromatic hydrocarbons and any combination thereof and more preferably from aromatic hydrocarbons).

In another embodiment, the catalyst is selected from cesium halides, cesium carbonates, cesium hydroxide and any combination thereof (preferably from cesium halides, cesium carbonates and any combination thereof and in particular from cesium halides) and the inert organic solvent S1 is selected from aliphatic hydrocarbons, aromatic hydrocarbons, halogenated aliphatic hydrocarbons, halogenated aromatic hydrocarbons and any combination thereof (preferably from aliphatic hydrocarbons, aromatic hydrocarbons and any combination thereof and more preferably from aromatic hydrocarbons).

In another embodiment, the catalyst is selected from rubidium chloride, cesium chloride, rubidium carbonate, cesium carbonate, rubidium hydroxide, cesium hydroxide and any combination thereof (preferably from rubidium chloride, cesium chloride, rubidium carbonate, cesium carbonate and any combination thereof and more preferably from rubidium chloride, cesium chloride or a combination thereof) and the inert organic solvent S1 is selected from aliphatic hydrocarbons, aromatic hydrocarbons, halogenated aliphatic hydrocarbons, halogenated aromatic hydrocarbons and any combination thereof (preferably from aliphatic hydrocarbons, aromatic hydrocarbons and any combination thereof and more preferably from aromatic hydrocarbons).

In another embodiment, the catalyst is selected from rubidium chloride, rubidium carbonate, rubidium hydroxide and any combination thereof (preferably from rubidium chloride, rubidium carbonate and any combination thereof and in particular rubidium chloride) and the inert organic solvent S1 is selected from aliphatic hydrocarbons, aromatic hydrocarbons, halogenated aliphatic hydrocarbons, halogenated aromatic hydrocarbons and any combination thereof (preferably from aliphatic hydrocarbons, aromatic hydrocarbons and any combination thereof and more preferably from aromatic hydrocarbons).

In another embodiment, the catalyst is selected from cesium chloride, cesium carbonate, cesium hydroxide and any combination thereof (preferably from cesium chloride, cesium carbonate and any combination thereof and in particular cesium chloride) and the inert organic solvent S1 is selected from aliphatic hydrocarbons, aromatic hydrocarbons, halogenated aliphatic hydrocarbons, halogenated aromatic hydrocarbons and any combination thereof (preferably from aliphatic hydrocarbons, aromatic hydrocarbons and any combination thereof and more preferably from aromatic hydrocarbons).

In another embodiment, the catalyst is selected from rubidium chloride, cesium chloride, rubidium carbonate, cesium carbonate, rubidium hydroxide, cesium hydroxide and any combination thereof (preferably from rubidium chloride, cesium chloride, rubidium carbonate, cesium carbonate and any combination thereof and more preferably from rubidium chloride, cesium chloride or a combination thereof) and the inert organic solvent S1 is selected from n-heptane, n-octane, n-nonane, n-decane, toluene, o-xylene, m-xylene, p-xylene, ethylbenzene, 1,3,5-trimethylbenzene (mesitylene), methylene chloride, chlorobenzene and any combination thereof (preferably from n-heptane, n-octane, toluene, o-xylene, m-xylene, p-xylene, ethylbenzene, 1,3,5-trimethylbenzene (mesitylene), chlorobenzene, and any combination thereof, more preferably from n-heptane, toluene, o-xylene, m-xylene, p-xylene and any combination thereof and in particular toluene).

In another embodiment, the catalyst is selected from rubidium chloride, rubidium carbonate, rubidium hydroxide and any combination thereof (preferably from rubidium chloride, rubidium carbonate and any combination thereof and in particular rubidium chloride) and the inert organic solvent S1 is selected from n-heptane, n-octane, n-nonane, n-decane, toluene, o-xylene, m-xylene, p-xylene, ethylbenzene, 1,3,5-trimethylbenzene (mesitylene), methylene chloride, chlorobenzene and any combination thereof (preferably from n-heptane, n-octane, toluene, o-xylene, m-xylene, p-xylene, ethylbenzene, 1,3,5-trimethylbenzene (mesitylene), chlorobenzene, and any combination thereof, more preferably from n-heptane, toluene, o-xylene, m-xylene, p-xylene and any combination thereof and in particular toluene).

In another embodiment, the catalyst is selected from cesium chloride, cesium carbonate, cesium hydroxide and any combination thereof (preferably from cesium chloride, cesium carbonate and any combination thereof and in particular cesium chloride) and the inert organic solvent S1 is selected from n-heptane, n-octane, n-nonane, n-decane, toluene, o-xylene, m-xylene, p-xylene, ethylbenzene, 1,3,5-trimethylbenzene (mesitylene), methylene chloride, chlorobenzene and any combination thereof (preferably from n-heptane, n-octane, toluene, o-xylene, m-xylene, p-xylene, ethylbenzene, 1,3,5-trimethylbenzene (mesitylene), chlorobenzene, and any combination thereof, more preferably from n-heptane, toluene, o-xylene, m-xylene, p-xylene and any combination thereof and in particular toluene).

In another embodiment, the inert organic solvent S1 has a boiling point at atmospheric pressure (1 bar) of from 35 to 200° C., preferably from 90 to 165° C. and more preferably from 100 to 150° C.

The molar ratio of the inert organic solvent S1 to (±)-2-exo-hydroxy-1-methyl-4-isopropyl-7-oxa-bicyclo[2.2.1] heptane of the formula (II), any one of its individual enantiomers or any non-racemic mixture thereof, in particular (±)-2-exo-hydroxy-1-methyl-4-isopropyl-7-oxabicyclo [2.2.1]heptane of the formula (II), can vary widely and depends on the reaction conditions used, but is generally from 30:1 to 1:1, preferably from 15:1 to 1:1, more preferably from 10:1 to 1:1 and even more preferably from 5:1 to 1:1.

In another embodiment, the molar ratio of toluene to (±)-2-exo-hydroxy-1-methyl-4-isopropyl-7-oxabicyclo [2.2.1]heptane of the formula (II), any one of its individual enantiomers or any non-racemic mixture thereof, in particular (±)-2-exo-hydroxy-1-methyl-4-isopropyl-7-oxabicyclo [2.2.1]heptane of the formula (II), is 10:1 to 1:1, preferably 5:1 to 2:1 and more preferably 4:1 to 3:1.

In cases where the process of this invention is conducted in the presence of at least one base capable of forming a solvent S2 selected from water, a $C_1$-$C_4$ alkyl alcohol or any combination thereof under the reaction conditions, the process of this invention preferably further comprises the step of simultaneously removing the solvent S2 (preferably water, methanol, ethanol, iso-propanol, tert-butanol or any combination thereof, more preferably water, methanol, ethanol, tert-butanol or any combination thereof, even more preferably water, methanol or a combination thereof and in particular water) from the reaction mixture (hereinafter also referred to as "further step").

The optional removal of water and/or the $C_1$-$C_4$ alkyl alcohol allows an even better suspension of salts formed during the reaction in the reaction medium as finely divided particles. Therefore, fouling on reactor surfaces is further reduced. Further advantages include (1) better recovery and recycling of the inert organic solvent S1 used in this invention; (2) further reduction of side-component formation; and (3) further improvement in yield of the desired (±)-2-exo-(2-Methylbenzyloxy)-1-methyl-4-isopropyl-7-oxabicyclo [2.2.1]heptane of the formula (I), any of its individual enantiomers or any non-racemic mixture thereof.

In a preferred embodiment, the solvent S2 (preferably water, methanol, ethanol, iso-propanol, tert-butanol or any combination thereof, more preferably water, methanol, ethanol, tert-butanol or any combination thereof, even more preferably water, methanol or a combination thereof and in particular water) is simultaneously and continuously or simultaneously and intermittently (more preferably simultaneously and continuously) removed from the reaction mixture during the reaction.

By "continuously removed" or "continuous removal" it is meant that the solvent S2 is substantially or completely continuously removed from the reaction mixture as the reaction progresses. In this regard, "continuous" or "continuously" are not meant in any way to exclude normal interruptions in the continuity of the removal step due to, for example, start-up of the process.

The removal of the solvent S2 can be achieved by various methods known in the art, such as, for example, chemical or physicochemical methods. As chemical methods, the addition of chemical scavengers or drying reagents (e.g. sodium sulfate, magnesium sulfate, molecular sieves, zeolites or calcium oxide) may be used. Physicochemical methods include but are not limited to membrane separation processes (e.g. nanofiltration) or azeotropic distillation.

In a preferred embodiment, the solvent S2 (preferably water, methanol, ethanol, iso-propanol, tert-butanol or any combination thereof, more preferably water, methanol, ethanol, tert-butanol or any combination thereof, even more preferably water, methanol or a combination thereof and in particular water) is removed from the reaction mixture by azeotropic distillation. In particular, the solvent S2 (preferably water, methanol, ethanol, iso-propanol, tert-butanol or any combination thereof, more preferably water, methanol, ethanol, tert-butanol or any combination thereof, even more preferably water, methanol or a combination thereof and in particular water) is removed from the reaction mixture as an azeotrope formed by the inert organic solvent S1 and the solvent S2.

In particular, the inert organic solvent S1 is capable of forming an azeotrope with the solvent S2.

In yet another embodiment, the inert organic solvent S1 is capable of forming an azeotrope with the solvent S2 selected from water, a $C_1$-$C_4$ alkyl alcohol or any combination thereof (preferably water, methanol, ethanol, iso-propanol, tert-butanol or any combination thereof, more preferably water, methanol, ethanol, tert-butanol or any combination thereof, even more preferably water, methanol or a combination thereof and in particular water).

In one embodiment, the inert organic solvent S1 is capable of forming an azeotrope with the solvent S2 which is water.

In another embodiment, the inert organic solvent S1 is capable of forming an azeotrope with the solvent S2 selected from $C_1$-$C_4$ alkyl alcohols (preferably methanol, ethanol, iso-propanol, tert-butanol or any combination thereof, more preferably methanol, ethanol, tert-butanol or any combination thereof and in particular methanol).

In order to balance the potential loss of the inert organic solvent S1 removed by the azeotropic distillation in the reaction mixture, fresh inert organic solvent S1, recycled inert organic solvent S1 or a mixture comprising the inert organic solvent S1 and having a lower concentration of the solvent S2 as compared to the azeotrope can be added to the reaction mixture during the reaction.

Thus, in a preferred embodiment, the solvent S2 is simultaneously (preferably simultaneously and continuously) removed from the reaction mixture as an azeotrope formed by the inert organic solvent S1 and the solvent S2, and the inert organic solvent S1 or a mixture comprising the inert organic solvent S1 and having a lower concentration of the solvent S2 as compared to the azeotrope is added to the reaction mixture during the reaction. The inert organic solvent S1 (either fresh inert organic solvent S1, recycled inert organic solvent S1 or a combination thereof) or a mixture comprising the inert organic solvent S1 and having a lower concentration of water, the $C_1$-$C_4$ alkyl alcohol or any mixture thereof as compared to the azeotrope may be added to the reaction mixture continuously or periodically (preferably continuously) during the reaction.

The inert organic solvent S1 (either fresh inert organic solvent S1, recycled inert organic solvent S1 or a combination thereof) or a mixture comprising the inert organic solvent S1 and having a lower concentration of water, the $C_1$-$C_4$ alkyl alcohol or any mixture thereof as compared to the azeotrope may preferably added to the reaction mixture in an amount such that the initial volume of the reaction mixture or a volume which is less than the initial volume of the reaction mixture (e.g. 90% or 80% or 70% or 60% or 50% or 40% or 30% as compared to the initial volume of the reaction mixture) is maintained during the reaction. The inert organic solvent S1 (either fresh inert organic solvent S1, recycled inert organic solvent S1 or a combination thereof) or a mixture comprising the inert organic solvent S1 and having a lower concentration of water, the $C_1$-$C_4$ alkyl alcohol or any mixture thereof as compared to the azeotrope may also be added in an amount such that a volume which is higher than the initial volume of the reaction mixture is obtained.

In a preferred embodiment, the further step comprises the steps of
(i) distilling the azeotrope formed by the inert organic solvent S1 and water,
(ii) continuously condensing and separating the azeotrope into an organic solvent phase and a water phase,
(iii) recycling the organic solvent phase to the reaction mixture, and
(iv) removing the water phase from the process.

In a particularly preferred embodiment, the further step comprises the steps of
(i.1) removing the azeotrope formed by the inert organic solvent S1 and water as a vapor fraction from the reaction mixture,
(ii.1) condensing said vapor fraction to form a biphasic condensate and passing said biphasic condensate through a phase separator to form an organic solvent phase and a water phase,
(iii.1) transferring the inert organic solvent phase (preferably via overflow) to the reaction mixture, and
(iv.1) removing the water phase from the process.

The process of the present invention may optionally be carried out in the presence of at least one phase-transfer catalyst.

Phase transfer catalysts suitable for use in the process of this invention are those well known in the art such as, for example, quaternary ammonium salts. Examples of suitable phase-transfer catalysts are trimethyl(phenyl) ammonium chloride, bromide, iodide or hydroxide and tetra-n-$C_1$-$C_{12}$-alkyl-ammonium chlorides, bromides, iodides or hydroxides, preferably tetra-n-$C_1$-$C_8$-alkyl-ammonium chlorides, bromides, iodides or hydroxides, e.g. tetramethylammonium chloride, bromide, iodide or hydroxide, tetraethylammonium chloride, bromide, iodide or hydroxide, tetra-n-propylammonium chloride, bromide, iodide or hydroxide, tetra-n-butylammonium chloride, bromide, iodide or hydroxide, tetra-n-pentylammonium chloride, bromide, iodide or hydroxide, tetra-n-hexylammonium chloride, bromide, iodide or hydroxide, tetra-n-heptylammonium chloride, bromide, iodide or hydroxide, tetra-n-octylammonium chloride, bromide, iodide or hydroxide, methyl-tri-n-butylammonium chloride, bromide, iodide or hydroxide, ethyl-tri-methylammonium chloride, bromide, iodide or hydroxide, n-propyl-trimethyl ammonium chloride, bromide, iodide or hydroxide, methyl-triethyl ammonium chloride, bromide, iodide or hydroxide and n-butyl-tri-ethylammonium chloride, bromide, iodide or hydroxide. Of these, the use of tetra-n-$C_1$-$C_4$-alkyl-ammonium chlorides, bromides, iodides or hydroxides is preferred, in particular tetra-n-butylammonium chloride, bromide, iodide or hydroxide and methyl-tri-n-butylammonium chloride, bromide, iodide or hydroxide. The phase-transfer catalysts, which are usually solid in pure form, can be used as such or, preferably, in dissolved form. An effective amount of the phase-transfer catalyst may range from 0.001 to 0.5 molar equivalents, preferably 0.001 to 0.2 molar equivalents relative to (±)-2-exo-hydroxy-1-methyl-4-isopropyl-7-oxabicyclo[2.2.1]heptane (II), any one of its individual enantiomers or any non-racemic mixture thereof, in particular (±)-2-exo-hydroxy-1-methyl-4-isopropyl-7-oxabicyclo[2.2.1]heptane (II).

The process of the present invention can be carried out under atmospheric pressure or under slightly elevated or reduced pressure. Typically, the atmospheric pressure is employed. In another embodiment, the process of this invention is conducted under reduced pressure, preferably in a range of from 0.01 to 10 bar, preferably 0.1 to 6 bar.

The temperature used in the process of the present invention can vary widely and depends on a variety of factors such as, for example, the inert organic solvent S1 and the pressure used. Under atmospheric pressure (1 bar), the temperature is generally from 35 to 200° C., preferably from 70 to 170° C., more preferably from 80 to 150° C. and even more preferably from 110 to 135° C.

The reaction time can vary in a wide range and depends on a variety of factors such as, for example, temperature, pressure, or the reagents and auxiliary substances used. Typical reaction times are in the range of from 10 to 50 hours, preferably from 10 to 30 hours and more preferably from 10 to 20 hours.

In the process of this invention, the reaction mixture comprising (±)-2-exo-hydroxy-1-methyl-4-isopropyl-7-oxabicyclo[2.2.1]heptane of the formula (II), any of its individual enantiomers or any non-racemic mixture thereof (preferably (±)-2-exo-hydroxy-1-methyl-4-isopropyl-7-oxabicyclo[2.2.1]heptane of the formula (II)), the 2-Methylbenzyl compound of the formula (III), the base as defined herein, the catalyst as defined herein and the inert organic solvent S1 as defined herein may first be provided, and the reaction mixture is then heated to reflux.

In another embodiment, a first mixture comprising (±)-2-exo-hydroxy-1-methyl-4-isopropyl-7-oxabicyclo[2.2.1]heptane of the formula (II), any of its individual enantiomers or any non-racemic mixture thereof (preferably (±)-2-exo-hydroxy-1-methyl-4-isopropyl-7-oxabicyclo[2.2.1]heptane of the formula (II)), the base as defined herein, the catalyst as defined herein and the inert organic solvent S1 as defined herein is provided, the first mixture is heated to reflux, and the 2-Methylbenzyl compound of the formula (III) is added to the first mixture under agitation to form the reaction mixture.

In case the 2-Methylbenzyl compound of the formula (III) wherein X is an ammonium group of the formula (IV) (such as e.g. trimethyl(o-tolylmethyl)ammonium chloride of the formula (IIIf) or triethyl(o-tolylmethyl)ammonium chloride of the formula (IIIg)) is formed in-situ as described herein, a first mixture comprising (±)-2-exo-hydroxy-1-methyl-4-isopropyl-7-oxabicyclo[2.2.1]heptane of the formula (II), any of its individual enantiomers or any non-racemic mixture thereof (preferably (±)-2-exo-hydroxy-1-methyl-4-isopropyl-7-oxabicyclo[2.2.1]heptane of the formula (II)), the base as defined herein, the catalyst as defined herein, the inert organic solvent S1 as defined herein and the tertiary amine of the formula $NR_1R_2R_3$ wherein $R_1$, $R_2$ and $R_3$ have the same meaning as in formula (IV) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl) is provided, the first mixture heated to reflux, and the 2-Methylbenzyl compound of the formula (III) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) is added to the first mixture under agitation to form the reaction mixture.

The molar ratio of the tertiary amine of the formula $NR_1R_2R_3$ (in particular trimethylamine, triethylamine or a combination thereof, more preferably trimethylamine) to the 2-Methylbenzyl compound of the formula (III)) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) may be from 1:1 to 0.1:1, preferably from 0.5:1 to 0.1:1, more preferably from 0.25:1 to 0.1:1, even more preferably from 0.15:1 to 0.1:1 and yet more preferably 0.1:1 to 0.01:1.

In the process of this invention, the base (in solid form, as an aqueous solution or as a combination thereof) can be added batch-wise (in one or more individual portions, preferably in one portion) or continuously metered in, with preference being given to the batch-wise addition.

The 2-Methylbenzyl compound of the formula (III) can be added batch-wise (in one or more individual portions) or continuously metered in, with preference being given to the continuous metered addition.

(±)-2-exo-(2-Methylbenzyloxy)-1-methyl-4-isopropyl-7-oxabicyclo[2.2.1]heptane of the formula (I), any of its individual enantiomers or any non-racemic mixture thereof (preferably (±)-2-exo-(2-Methylbenzyloxy)-1-methyl-4-isopropyl-7-oxabicyclo[2.2.1]heptane of the formula (I)) is preferably isolated from the final reaction mixture by employing conventional methods, for example by extraction, in particular extraction with a basic or neutral aqueous medium, distillation, and the like.

After completion of the reaction, the reaction mixture is preferably extracted with water followed by concentration and removal of the inert organic solvent S1. For further purification, thin-film-evaporation as well as rectification can be applied.

The invention is illustrated by the following examples without being limited thereto or thereby.

EXAMPLE 1

Preparation of (±)-2-exo-(2-Methylbenzyloxy)-1-methyl-4-isopropyl-7-oxabicyclo[2.2.1]heptane
(Base: Solid Sodium Hydroxide, Solvent: Toluene, 1 Molar Equivalent of 1-(chloromethyl)-2-methylbenzene, Catalyst: Cesium Chloride)

(±)-2-exo-hydroxy-1-methyl-4-isopropyl-7-oxabicyclo[2.2.1]heptane (38.0 g, 0.222 mol), solid sodium hydroxide (11.8 g, 0.289 mol) and 5 mol % cesium chloride (1.90 g, 0.011 mol) were suspended in toluene (71.6 g, 0.777 mol). The reaction mixture was heated to reflux (internal temperature 116° C.). At this temperature 1-(chloromethyl)-2-methyl-benzene (32.0 g, 0.222 mol) was dosed within 7 h to the mixture. The reaction mixture was kept for 24 h at reflux (internal temperature increases during reaction to 130° C.). After cooling of the reaction mixture to 25° C., water (70 g) was added, and the reaction mixture was extracted. After phase separation water (70 g) was added, again. The mixture was extracted and phases were separated. The product solution was distilled using Dean-Stark conditions. The product solution (163.2 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 31.1%. This corresponds to a yield of 83.3% of (±)-2-exo-(2-Methylbenzyloxy)-1-methyl-4-isopropyl-7-oxabicyclo[2.2.1]heptane. The yield based on recovered starting material ((±)-2-exo-hydroxy-1-methyl-4-isopropyl-7-oxabicyclo[2.2.1]heptane) corresponds to 97.1%.

COMPARATIVE EXAMPLE 1

Preparation of (±)-2-exo-(2-Methylbenzyloxy)-1-methyl-4-isopropyl-7-oxabicyclo[2.2.1]heptane
(Base: Solid Sodium Hydroxide, Solvent: Toluene, 1 Molar Equivalent of 1-(chloromethyl)-2-methylbenzene, Not According to the Invention)

(±)-2-exo-hydroxy-1-methyl-4-isopropyl-7-oxabicyclo[2.2.1]heptane (125.9 g, 0.736 mol), solid sodium hydroxide (39.0 g, 0.956 mol) were suspended in toluene (237.3 g, 2.575 mol). The reaction mixture was heated to reflux (internal temperature 116° C.). At this temperature 1-(chloromethyl)-2-methyl-benzene (106.1 g, 0.736 mol) was dosed within 7 h to the mixture. The reaction-mixture was kept for 24 h at reflux (internal temperature increases during reaction to 130° C.). After cooling of the reaction mixture to 25° C., water (200 g) was added, and the reaction mixture was extracted. After phase separation water (201 g) was added, again. The mixture was extracted and phases were separated. The product solution was distilled using Dean-Stark conditions. The product solution (279.2 g) was analyzed via quantitative gas chromatography (GC) (GC with internal standard) and showed a (±)-2-exo-(2-Methylbenzyloxy)-1-methyl-4-iso-propyl-7-oxabicyclo[2.2.1]heptane concentration of 47.9%. This corresponds to a yield of 66.2% of (±)-2-exo-(2-Methylbenzyloxy)-1-methyl-4-isopropyl-7-oxabicyclo[2.2.1]heptane. The yield based on recovered starting material ((±)-2-exo-hydroxy-1-methyl-4-isopropyl-7-oxabicyclo[2.2.1]heptane) corresponds to 88.3%.

EXAMPLE 2

Preparation of (±)-2-exo-(2-Methylbenzyloxy)-1-methyl-4-isopropyl-7-oxabicyclo[2.2.1]heptane Using Removal of Water by Azeotropic Distillation (Base: Solid Sodium Hydroxide, Solvent: Toluene, 0.97 Molar Equivalent of 1-(chloromethyl)-2-methyl-benzene, 0.025 Molar Equivalents of Cesium Chloride)

(±)-2-exo-hydroxy-1-methyl-4-isopropyl-7-oxabicyclo [2.2.1]heptane (241.4 g, 1.411 mol), solid sodium hydroxide (74.9 g, 1.835 mol) and cesium chloride (6.00 g, 0.035 mmol) were suspended in toluene (455.5 g, 4.938 mol). The reaction mixture was heated to reflux (jacket temperature: 130° C.). At this temperature 1-(chloromethyl)-2-methyl-benzene (197.4 g, 1.369 mol) was dosed within 7 h to the mixture. The reaction mixture was kept for 24 h at reflux and the water was continuously removed from the reaction mixture via azeotropic distillation (Dean Stark conditions) during this time. After cooling of the reaction mixture to 70° C. and extraction, 2× with water (2×310.4 g), the product-solution was azeotropically dried using Dean-Stark conditions. The product solution (835.3 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 42.1%. This corresponds to a yield of 90.8% of (±)-2-exo-(2-Methylbenzyloxy)-1-methyl-4-isopropyl-7-oxabicyclo[2.2.1]heptane. The yield based on recovered starting material ((±)-2-exo-hydroxy-1-methyl-4-isopropyl-7-oxabicyclo[2.2.1]heptane) corresponds to >97.8%.

EXAMPLE 3

Preparation of (±)-2-exo-(2-Methylbenzyloxy)-1-methyl-4-isopropyl-7-oxabicyclo[2.2.1]heptane Using Removal of Water by Azeotropic Distillation (Base: Solid Sodium Hydroxide, Solvent: Toluene, 0.97 Molar Equivalent of 1-(chloromethyl)-2-methyl-benzene, 0.025 Molar Equivalents of Cesium Chloride)

(±)-2-exo-hydroxy-1-methyl-4-isopropyl-7-oxabicyclo [2.2.1]heptane (241.4 g, 1.411 mol), solid sodium hydroxide (74.9 g, 1.835 mol) and cesium chloride (6.00 g, 0.035 mmol) were suspended in toluene (455.5 g, 4.938 mol). The reaction mixture was heated to reflux (jacket temperature: 135° C.). At this temperature 1-(chloromethyl)-2-methyl-benzene (197.4 g, 1.369 mol) was dosed within 7 h to the mixture. The reaction mixture was kept at reflux for 24 h and the water was continuously removed from the reaction mixture via azeotropic distillation (Dean Stark conditions) during this time. After cooling of the reaction mixture to 70° C. and extraction, 2× with water (2×310.4 g), the product solution was azeotropically dried using Dean-Stark conditions. The product solution (722.8 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 48.3%. This corresponds to a yield of 90.2% of (±)-2-exo-(2-Methylbenzyloxy)-1-methyl-4-isopropyl-7-oxabicyclo[2.2.1]heptane. The yield based on recovered starting material ((±)-2-exo-hydroxy-1-methyl-4-isopropyl-7-oxabicyclo[2.2.1]heptane) corresponds to >98.0%.

EXAMPLE 4

Preparation of (±)-2-exo-(2-Methylbenzyloxy)-1-methyl-4-isopropyl-7-oxabicyclo[2.2.1]heptane Using Removal of Water by Azeotropic Distillation (Base: Solid Sodium Hydroxide, Solvent: Toluene, 0.97 Molar Equivalent of 1-(chloromethyl)-2-methyl-benzene, 0.035 Molar Equivalents of Cesium Chloride)

(±)-2-exo-hydroxy-1-methyl-4-isopropyl-7-oxabicyclo [2.2.1]heptane (212.8 g, 1.244 mol), solid sodium hydroxide (66.0 g, 1.617 mol) and cesium chloride (7.40 g, 0.044 mmol) were suspended in toluene (401.1 g, 4.353 mol). The reaction mixture was heated to reflux (jacket temperature: 135° C.). At this temperature 1-(chloromethyl)-2-methyl-benzene (174.0 g, 1.207 mol) was dosed within 7 h to the mixture. The reaction mixture was kept for 24 h at reflux and the water was continuously removed from the reaction mixture via azeotropic distillation (Dean-Stark conditions) during this time. After cooling of the reaction mixture to 70° C. and extraction, 3× with water (1×239.4 g; 1×263.5 g, 1×229.4 g), the product-solution was azeotropically dried using Dean-Stark conditions. The product solution (824.9 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 38.0%. This corresponds to a yield of 91.9% of (±)-2-exo-(2-Methylbenzyloxy)-1-methyl-4-isopropyl-7-oxabicyclo[2.2.1]heptane. The yield based on recovered starting material ((±)-2-exo-hydroxy-1-methyl-4-isopropyl-7-oxabicyclo[2.2.1]heptane) corresponds to >98.5%.

EXAMPLE 5

Preparation of (±)-2-exo-(2-Methylbenzyloxy)-1-methyl-4-isopropyl-7-oxabicyclo[2.2.1]heptane Using Removal of Water by Azeotropic Distillation (Base: Solid Sodium Hydroxide, Solvent: Toluene, 0.97 Molar Equivalent of 1-(chloromethyl)-2-methyl-benzene, 0.0125 Molar Equivalents of Cesium Carbonate)

(±)-2-exo-hydroxy-1-methyl-4-isopropyl-7-oxabicyclo [2.2.1]heptane (241.7 g, 1.413 mol), solid sodium hydroxide (75.0 g, 1.838 mol) and cesium carbonate (5.90 g, 0.018 mmol) were suspended in toluene (455.5 g, 4.944 mol). The reaction mixture was heated to reflux (jacket temperature 130° C.). At this temperature 1-(chloromethyl)-2-methyl-benzene (197.6 g, 1.370 mol) was dosed within 7 h to the mixture. The reaction mixture was kept for 24 h at reflux and the water was continuously removed from the reaction mixture via azeotropic distillation (Dean-Stark conditions) during this time. After cooling of the reaction mixture to 70° C. and extracted 3× with water, the product-solution was azeotropically dried using Dean-Stark conditions. The product solution (801.7 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 44.7%. This corresponds to a yield of 92.5% of (±)-2-exo-(2-Methylbenzyloxy)-1-methyl-4-isopropyl-7-oxabicyclo

[2.2.1]heptane. The yield based on recovered starting material ((±)-2-exo-hydroxy-1-methyl-4-isopropyl-7-oxabicyclo[2.2.1]heptane) corresponds to >99.5%.

EXAMPLE 6

Preparation of (±)-2-exo-(2-Methylbenzyloxy)-1-methyl-4-isopropyl-7-oxabicyclo[2.2.1]heptane Using Removal of Water by Azeotropic Distillation (Base: Solid Sodium Hydroxide, Solvent: Toluene, 0.97 Molar Equivalent of 1-(chloromethyl)-2-methyl-benzene, 0.025 Molar Equivalents of Cesiumhydroxyide-Monohydrate)

(±)-2-exo-hydroxy-1-methyl-4-isopropyl-7-oxabicyclo[2.2.1]heptane (241.4 g, 1.411 mol), solid sodium hydroxide (75.0 g, 1.838 mol) and cesiumhydroxide-monohydrat (6.30 g, 0.036 mmol) were suspended in toluene (455.5 g, 4.944 mol). The reaction mixture was heated to reflux (jacket temperature 130° C.). At this temperature 1-(chloromethyl)-2-methyl-benzene (197.4 g, 1.369 mol) was dosed within 7 h to the mixture. The reaction mixture was kept for 24 h at reflux and the water was continuously removed from the reaction mixture via azeotropic distillation (Dean Stark conditions) during this time. After cooling of the reaction mixture to 70° C. and extracted 3× with water, the product-solution was azeotropically dried using Dean-Stark conditions. The product solution (801.0 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 43.6%. This corresponds to a yield of 90.2% of (±)-2-exo-(2-Methylbenzyloxy)-1-methyl-4-isopropyl-7-oxabicyclo[2.2.1]heptane. The yield based on recovered starting material ((±)-2-exo-hydroxy-1-methyl-4-isopropyl-7-oxabicyclo[2.2.1]heptane) corresponds to >98.2%.

EXAMPLE 7

Preparation of (±)-2-exo-(2-Methylbenzyloxy)-1-methyl-4-isopropyl-7-oxabicyclo[2.2.1]heptane Using Removal of Water by Azeotropic Distillation (Base: Solid Sodium Hydroxide, Solvent: Toluene, 0.97 Molar Equivalent of 1-(chloromethyl)-2-methyl-benzene, 0.025 Molar Equivalents of Rubidium Chloride)

(±)-2-exo-hydroxy-1-methyl-4-isopropyl-7-oxabicyclo[2.2.1]heptane (241.7 g, 1.413 mol), solid sodium hydroxide (75.2 g, 1.842 mol) and rubidium chloride (4.30 g, 0.035 mmol) were suspended in toluene (455.3 g, 4.941 mol). The reaction mixture was heated to reflux. At this temperature 1-(chloromethyl)-2-methyl-benzene (197.4 g, 1.369 mol) was dosed within 7 h to the mixture. The reaction mixture was kept for 24 h at and the water was continuously removed from the reaction mixture via azeotropic distillation (Dean Stark conditions) during this time. After cooling of the reaction mixture to 70° C. and extracted 3× with water. The product-solution was then azeotropically dried using Dean-Stark conditions. The product solution (811.6 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 43.0%. This corresponds to a yield of 90.1% of (±)-2-exo-(2-Methylbenzyloxy)-1-methyl-4-isopropyl-7-oxabicyclo[2.2.1]heptane. The yield based on recovered starting material ((±)-2-exo-hydroxy-1-methyl-4-isopropyl-7-oxabicyclo[2.2.1]heptane) corresponds to >98.5%.

The invention claimed is:

1. A process for preparing (±)-2-exo-(2-Methylbenzyloxy)-1-methyl-4-isopropyl-7-oxabicyclo[2.2.1]heptane of the formula (I)

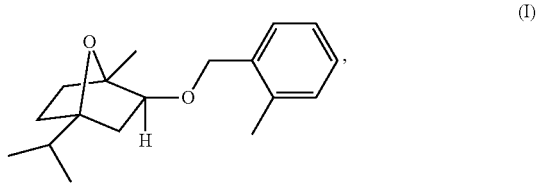 [SMILES: Cc1ccccc1COC1CC2(C(C)C)CCC1(C)O2]

any of its individual enantiomers or any non-racemic mixture thereof, comprising reacting (±)-2-exo-hydroxy-1-methyl-4-isopropyl-7-oxabicyclo[2.2.1]heptane of the formula (II)

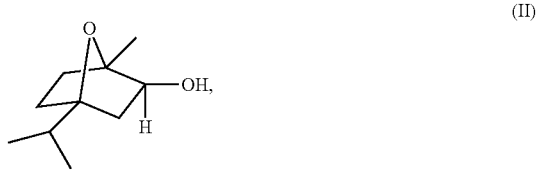

any of its individual enantiomers or any non-racemic mixture thereof, with a 2-methylbenzyl compound of the formula (III)

wherein X is a leaving group, in the presence of at least one base, at least one catalyst selected from rubidium salts, and cesium salts, or any combination thereof and at least one inert organic solvent S1.

2. The process according to claim 1 wherein X is selected from halogen and an oxygen linked leaving group.

3. The process according to claim 1 wherein X is halogen.

4. The process according to claim 1 wherein the base is selected from alkali metal and alkaline earth metal hydroxides, alkali metal and alkaline earth metal carbonates, alkali metal and alkaline earth metal hydrogen carbonates, alkali metal and alkaline earth metal oxides, and alkali metal and alkaline earth metal $C_1$-$C_4$ alcoholates, or any combination thereof, each alkali metal being independently selected from lithium, sodium and potassium, and each alkaline earth metal being independently selected from calcium, magnesium and barium.

5. The process according to claim 1 wherein the base is selected from lithium hydroxide, sodium hydroxide, and potassium hydroxide, or any combination thereof.

6. The process according to claim 1 wherein the catalyst is selected from rubidium and cesium salts of inorganic acids, and rubidium and cesium salts of organic acids, or any combination thereof.

7. The process according to claim 1 wherein the catalyst is selected from rubidium and cesium halides, rubidium and cesium carbonates, rubidium and cesium sulfates, rubidium and cesium nitrate, rubidium and cesium phosphates, rubidium and cesium oxide, rubidium and cesium hydroxide, rubidium and cesium carboxylates, rubidium and cesium $C_1$-$C_4$ alcoholates, and rubidium and cesium sulfonates, or any combination thereof.

8. The process according to claim 1 wherein the catalyst is added to the reaction mixture in solid form.

9. The process according to claim 1 wherein the inert organic solvent S1 is selected from non-polar solvents.

10. The process according to claim 1 wherein the inert organic solvent S1 is selected from aliphatic hydrocarbons, and aromatic hydrocarbons, or any combination thereof.

11. The process according to claim 1 wherein the inert organic solvent S1 is selected from n-heptane, n-octane, toluene, o-xylene, m-xylene, p-xylene, ethylbenzene, and 1,3,5-trimethylbenzene (mesitylene), or any combination thereof.

12. The process according to claim 1 wherein the base is capable of forming a solvent S2 selected from water, and a $C_1$-$C_4$ alkyl alcohol, or any combination thereof under the reaction conditions.

13. The process according to claim 12 further comprising the step of simultaneously removing the solvent S2 from the reaction mixture.

14. The process according to claim 1 wherein the 2-Methylbenzyl compound of the formula (III) is 2-methylbenzyl chloride of the formula (IIIa)

(IIIa)

* * * * *